(12) United States Patent
Tekamp-Olson

(10) Patent No.: US 6,706,496 B2
(45) Date of Patent: *Mar. 16, 2004

(54) METHOD FOR EXPRESSION OF HETEROLOGOUS PROTEINS IN YEAST

(75) Inventor: Patricia Tekamp-Olson, San Anselmo, CA (US)

(73) Assignee: Chiron Corporation, Emeryville, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/921,398

(22) Filed: Aug. 2, 2001

(65) Prior Publication Data

US 2002/0055169 A1 May 9, 2002

Related U.S. Application Data

(63) Continuation of application No. 09/528,108, filed on Mar. 17, 2000, now Pat. No. 6,312,923, which is a continuation of application No. 09/340,250, filed on Jul. 1, 1999, now Pat. No. 6,083,723, which is a continuation of application No. 08/989,251, filed on Dec. 12, 1997, now Pat. No. 6,017,731.
(60) Provisional application No. 60/032,720, filed on Dec. 13, 1996.

(51) Int. Cl.$^7$ ............................................. C12N 15/00
(52) U.S. Cl. .................. 435/69.4; 435/320; 435/254.2; 536/23.1; 536/24.1
(58) Field of Search ............................. 536/23.1, 24.1; 530/351; 435/320.1, 325, 254.2, 69.4

(56) References Cited

U.S. PATENT DOCUMENTS

| | | |
|---|---|---|
| 4,766,073 A | 8/1988 | Murray et al. |
| 4,769,328 A | 9/1988 | Murray et al. |
| 4,801,542 A | 1/1989 | Murray et al. |
| 4,845,075 A | 7/1989 | Murray et al. |
| 4,849,407 A | 7/1989 | Murray et al. |
| 4,889,919 A | 12/1989 | Murray et al. |
| 5,010,003 A | 4/1991 | Chang et al. |
| 5,045,633 A | 9/1991 | Murray et al. |
| 5,128,321 A | 7/1992 | Murray et al. |
| 5,187,263 A | 2/1993 | Murray et al. |
| 5,219,759 A | 6/1993 | Heldin et al. |
| 5,516,896 A | 5/1996 | Murray et al. |
| 5,602,034 A | 2/1997 | Tekamp-Olson |
| 6,083,723 A * | 7/2000 | Tekamp-Olson ........... 435/69.4 |
| 6,312,923 B1 * | 11/2001 | Tekamp-Olson ........... 435/69.1 |

FOREIGN PATENT DOCUMENTS

| | | |
|---|---|---|
| EP | 0 206 783 A2 | 12/1986 |
| EP | 0 324 274 A1 | 7/1989 |
| EP | 0 487 116 A1 | 5/1992 |
| WO | WO 90/10075 A1 | 9/1990 |
| WO | WO 92/11378 A1 | 7/1992 |
| WO | WO 95/02059 A1 | 1/1995 |
| WO | WO 95/34666 A1 | 12/1995 |
| WO | WO 95/35384 A1 | 12/1995 |
| WO | WO 97/22706 | 6/1997 |

OTHER PUBLICATIONS

Romanos et al., Foreign gene expression in yeast: a review, 1992, Yeast, vol. 8, pp. 423–488.*

Beer, H.D., et al., "The Folding and Activity of the Extracellular Lipase of *Rhizopus oryzae* Are Modulated by a Prosequence," *Biochem. J.*, 1996, pp. 351–359, vol. 319.

Brake, A.J., et al., "Alpha Factor–directed Synthesis and Secretion of Mature Foreign Proteins in *Saccharomyces cerevisiae*," *Proc. Natl. Acad. Sci. USA*, Aug. 1984, pp. 4642–4646, vol. 81.

Fabre, E., et al., "Role of the Proregion in the Production and Secretion of the *Yarrowia lipolytica* Alkaline Extracellular Protease," *The Journal of Biological Chemistry*, Feb. 25, 1991, pp. 3782–3790, vol. 266(6).

Fukuda, R., et al., "The Prosequence of *Rhizopus niveus* Aspartic Proteinase–I Supports Correct Folding and Secretion of Its Mature Part in *Saccharomyces cerevisiae*," *The Journal of Biological Chemistry*, Apr. 1, 1994, pp. 9556–9561, vol. 269(12).

Gray, A.M., and A.J. Mason, "Requirement for Activin A and Transforming Growth Factor—Beta 1 Pro–Regions in Homodimer Assembly," *Science*, Mar. 16, 1990, pp. 1328–1330, vol. 247.

Östman, A., et al., "Synthesis and Assembly of a Functionally Active Recombinant Platelet–derived Growth Factor AB Heterodimer," *The Journal of Biological Chemistry*, 1988, pp. 16202–16208, vol. 263(31), The American Society for Biochemistry and Molecular Biology, Inc., USA.

(List continued on next page.)

*Primary Examiner*—David Guzo
*Assistant Examiner*—Celine Qian
(74) *Attorney, Agent, or Firm*—Robert P. Blackburn; Lisa E. Alexander; Leslie T. Henry

(57) ABSTRACT

Compositions and methods for expression of heterologous mammalian proteins and their secretion in the biologically active mature form using a yeast host cell as the expression system are provided. Compositions of the invention are nucleotide sequences encoding a signal peptide sequence for a yeast secreted protein, an optional leader peptide sequence for a yeast secreted protein, a native propeptide leader sequence for a mature protein of interest, and a sequence for the mature protein of interest, all operably linked to a yeast promoter. Each of these elements is associated with a processing site recognized in vivo by a yeast proteolytic enzyme. Any or all of these processing sites may be a preferred processing site that has been modified or synthetically derived for more efficient cleavage in vivo. The compositions are useful in methods for expression of heterologous mammalian proteins and their secretion in the biologically active mature form. Particularly, vectors comprising these nucleotide coding sequences can be used to transform a yeast host cell, which can then be cultured and screened for secretion of the biologically active mature protein of interest.

15 Claims, 6 Drawing Sheets

OTHER PUBLICATIONS

Perez, C., et al., "A Nonsecretable Cell Surface Mutant of Tumor Necrosis Factor (TNF) Kills by Cell–to–Cell Contact," *Cell*, Oct. 19, 1990, pp. 251–258, vol. 63.

Raines, E., et al., "Biologic Activity of PDGF–related Sequences Expressed in Yeast," *Journal of Cellular Biochemistry*, 1985, p. 136, Suppl. 9A, Abstract No. 0338.

Sharma, S.K., et al., "Folding and Activation of Recombinant Human Prorenin," *Biotechnology and Applied Biochemistry*, 1987, pp. 181–193, vol. 9.

Smith, et al., "Heterologous Protein Secretion from Yeast," *Science*, Sep. 20, 1985, pp. 1219–1223, vol. 229.

Van den Berg., J., et al., "Kluyveromyces as a Host for Heterologous Gene Expression: Expression and Secretion of Prochymosin," *Biotechnology*, Feb. 1990, pp. 135–139, vol. 8.

Wiren, K., et al., "Importance of the Propeptide Sequence of Human Preproparathyroid Hormone for Signal Sequence Function," *The Journal of Biological Chemistry*, Dec. 25, 1988, pp. 19771–19777, vol. 263(36).

* cited by examiner

METHOD FOR EXPRESSION OF HETEROLOGOUS PROTEINS IN YEAST

CROSS-REFERENCE TO RELATED APPLICATIONS

The present application is a continuation of U.S. application Ser. No. 09/528,108, filed Mar. 17, 2000, now U.S. Pat. No. 6,312,923 which is a continuation of U.S. application Ser. No. 09/340,250, filed Jul. 1, 1999, now U.S. Pat. No. 6,083,723, which is a continuation of U.S. application Ser. No. 08/989,251, filed Dec. 12, 1997, now U.S. Pat. No. 6,017,731, which claims the benefit of U.S. Provisional Application Serial No. 60/032,720, filed Dec. 13, 1996, herein incorporated by reference in their entirety.

FIELD OF THE INVENTION

The present invention relates to the production of recombinant proteins using yeast host cells as the expression system. More particularly, it relates to compositions and methods for expression of heterologous proteins and their secretion as the biologically active mature proteins.

BACKGROUND OF THE INVENTION

Yeast host expression systems have been used to express and secrete proteins foreign to yeast. Numerous approaches have been developed in terms of the degree of expression and the yield of biologically active mature proteins.

Such approaches have involved modifications to the various molecular components that are involved in expression and secretion of proteins in yeast. These components include the translation and termination regulatory regions for gene expression; signal peptide and secretion leader peptide sequences, which direct the precursor form of the heterologous protein through the yeast secretory pathway; and processing sites, which cleave leader peptide sequences from the polypeptide sequence of the protein of interest.

Expression of the protein of interest can be enhanced with use of yeast-recognized regulatory regions. Increased yield of the heterologous protein of interest is commonly achieved with the use of yeast-derived signal and secretion leader peptide sequences. The use of native signal-leader peptide sequences is believed to improve direction of the protein of interest through the secretory pathway of the yeast host.

Previous work has demonstrated that full-length yeast α-factor signal-leader sequences can be used to drive expression and processing of heterologous proteins in yeast host cells. Substantial improvements in efficiency of expression can be accomplished with the use of truncated α-factor leader sequences, particularly for heterologous proteins that are poorly expressed by the full-length sequence or whose expression is nonresponsive to the full-length sequence.

Although the various approaches available in the art have been shown to work with some proteins, problems persist with post-translational processing. Often the amount of protein secreted is unacceptably low or incorrect processing leads to inactive forms of the protein. This is particularly true for proteins that are initially expressed as a precursor polypeptide sequence and whose assumption of a native conformation is facilitated by the presence of a native propeptide sequence in the precursor polypeptide.

Methods for expression of heterologous proteins and their secretion in a biologically active mature form using a yeast host cell as the expression system are needed.

SUMMARY OF THE INVENTION

Compositions and methods for expression of heterologous proteins, more particularly heterologous mammalian proteins, and their secretion in a biologically active mature form using a yeast host cell as the expression system are provided. Compositions of the invention are nucleotide sequences encoding a signal sequence for a yeast secreted protein, a native propeptide leader sequence for a mature protein of interest, and a peptide sequence for the mature protein of interest. Each of these elements is associated with a processing site recognized in vivo by a yeast proteolytic enzyme. Any or all of these processing sites may be a preferred processing site that has been modified or synthetically derived for more efficient cleavage in vivo. In turn, all of these elements are operably linked to a yeast promoter and optionally other regulatory sequences.

The nucleotide coding sequences of these compositions may additionally comprise a leader peptide sequence for a yeast secreted protein. When present, this element, which is also associated with a processing site recognized in vivo by a yeast proteolytic enzyme, is positioned 3' to the yeast signal sequence and 5' to the sequence for the mature protein of interest. Thus cleavage by a yeast proteolytic enzyme removes the yeast leader sequence from the hybrid precursor molecule comprising the sequence for the mature protein of interest.

These compositions are useful in methods for expression of heterologous mammalian proteins and their secretion in the biologically active mature form. Particularly, vectors comprising these nucleotide coding sequences can be used to transform a yeast host cell, which can then be cultured and screened for secretion of the biologically active mature protein of interest.

The method of the present invention is particularly useful in production of mammalian proteins whose assumption of a native confirmation is facilitated by the presence of a native propeptide sequence in the precursor polypeptide.

DETAILED DESCRIPTION OF THE INVENTION

Figure 1:
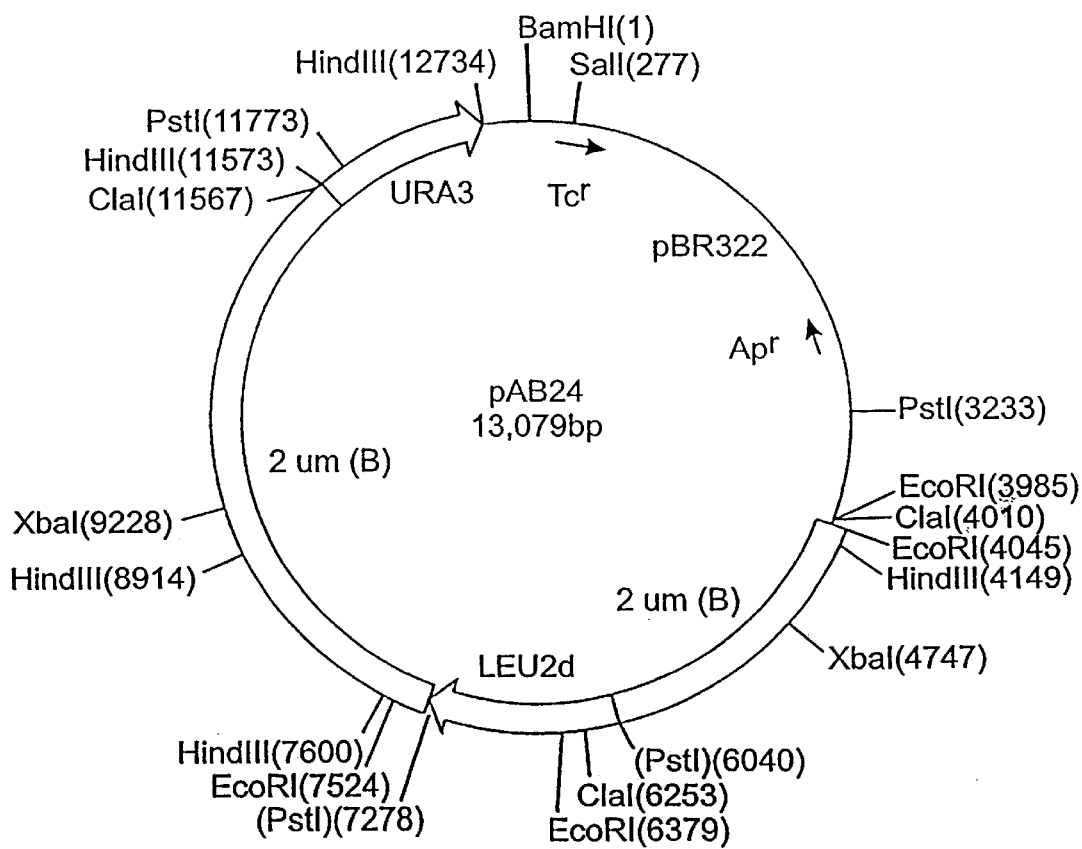
FIG. 1 is a map of plasmid pAB24.

The present invention provides compositions and methods for expression of heterologous proteins of interest, more particularly heterologous mammalian proteins, and their secretion in a biologically active mature form using a yeast host cell as the expression system. By "biologically active mature form" is intended a protein whose conformational form is similar to the native conformation such that its biological activity is substantially the same as the biological activity of the native protein.

Compositions of the present invention are nucleotide sequences encoding hybrid precursor polypeptides that each comprise the polypeptide sequence for a mature heterologous protein of interest. Expression vectors comprising these nucleotide sequences, all under the operational control of a yeast promoter region and a yeast terminator region, are also provided. Methods of the invention comprise stably transforming a yeast host cell with said vectors, where expression of the nucleotide sequence encoding the hybrid precursor polypeptide leads to secretion of the mature heterologous protein of interest in a biologically active form.

By "heterologous protein of interest" is intended a protein that is not expressed by the yeast host cell in nature. Preferably the heterologous protein will be a mammalian protein, including substantially homologous and functionally equivalent variants thereof. By "variant" is intended a polypeptide derived from the native polypeptide by deletion (so-called truncation) or addition of one or more amino acids to the N-terminal and/or C-terminal end of the native protein; deletion or addition of one or more amino acids at one or more sites in the native polypeptide; or substitution of one or more amino acids at one or more sites in the native polypeptide. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native polypeptide of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (Cold Spring Harbor Laboratory Press, Plainview, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇔Ala, Val⇔Ile⇔Leu, Asp⇔Glu, Lys⇔Arg, Asn⇔Gln, and Phe⇔Trp⇔Tyr.

In constructing variants of the protein of interest, modifications will be made such that variants continue to possess the desired activity. Obviously, any mutations made in the DNA encoding the variant protein must not place the sequence out of reading frame and preferably will not create complementary regions that could produce secondary mRNA structure. See EP Patent Application Publication No. 75,444.

Thus proteins of the invention include the naturally occurring forms as well as variants thereof These variants will be substantially homologous and functionally equivalent to the native protein. A variant of a native protein is "substantially homologous" to the native protein when at least about 80%, more preferably at least about 90%, and most preferably at least about 95% of its amino acid sequence is identical to the amino acid sequence of the native protein. A variant may differ by as few as 1, 2, 3, or 4 amino acids. By "functionally equivalent" is intended that the sequence of the variant defines a chain that produces a protein having substantially the same biological activity as the native protein of interest. Such functionally equivalent variants that comprise substantial sequence variations are also encompassed by the invention. Thus a functionally equivalent variant of the native protein will have a sufficient biological activity to be therapeutically useful. By "therapeutically useful" is intended effective in achieving a therapeutic goal, as, for example, healing a wound.

Methods are available in the art for determining functional equivalence. Biological activity can be measured using assays specifically designed for measuring activity of the native protein, including assays described in the present invention. Additionally, antibodies raised against the biologically active native protein can be tested for their ability to bind to the functionally equivalent variant, where effective binding is indicative of a protein having a conformation similar to that of the native protein.

The nucleotide sequences encoding the mature heterologous proteins of interest can be sequences cloned from non-yeast organisms, or they may be synthetically derived sequences, usually prepared using yeast-preferred codons. Examples of heterologous proteins suitable for the invention include, but are not limited to transforming growth factor (TGF-alpha and TGF-beta), somatostatin (as in SRIF 1), parathyroid hormone, and more particularly platelet-derived growth factor (PDGF) and insulin growth factor (IGF), all of which have a native prosequence as part of the precursor protein.

Thus compositions of the present invention are nucleotide sequences encoding hybrid precursor polypeptides that each comprise the polypeptide sequence for a mature heterologous protein of interest or any substantially homologous and functionally equivalent variants thereof. More particularly, nucleotide sequences of the present invention encode in the 5' to 3' direction a hybrid precursor polypeptide comprising the following primary elements:

$$5'\text{-SP-(PS)}_{n-1}\text{-(LP-PS)}_{n-2}\text{-(NPRO}_{MHP}\text{-PS)}_{n-3}\text{-MHP-(PS-CPRO}_{MHP})_{n-3}\text{'-3'}$$

wherein:
SP comprises a signal peptide sequence for a yeast secreted protein;
PS comprises a processing site cleaved in vivo by a yeast proteolytic enzyme;
LP comprises a leader peptide sequence for a yeast secreted protein;
$NPRO_{MHP}$ comprises a native N-terminal propeptide sequence of a mature heterologous protein of interest;
MHP comprises a peptide sequence for said mature heterologous mammalian protein of interest;
$CPRO_{MHP}$ comprises a native C-terminal propeptide sequence of said mature heterologous mammalian protein of interest; and
n–1, n–2, n–3, and n–4 independently=0 or 1;
wherein said processing sites allow for proteolytic processing of said precursor polypeptide to said mature protein in vivo by a yeast host cell, and wherein at least n–3 or n–4=1.

As is the case for the heterologous protein of interest, each of the other elements present in the hybrid precursor polypeptide can be a known naturally occurring polypeptide sequence or can be synthetically derived, including any variants thereof that do not adversely affect the function of the element as described herein. By "adversely affect" is intended inclusion of the variant form of the element results in decreased yield of the secreted mature heterologous protein of interest relative to the hybrid precursor polypeptide comprising the native form of the element.

In constructing the nucleotide sequence encoding the hybrid precursor polypeptide, it is within skill in the art to employ adapters or linkers to join the nucleotide fragments encoding the various elements of the precursor polypeptide. See, for example, Sambrook et al. (1989) *Molecular Cloning: A Laboratory Manual* (Cold Spring Harbor Laboratory Press, Plainview, N.Y.). Thus, the hybrid precursor polypeptide may comprise additional elements positioned 5' or 3' to any of the primary elements listed above, including the yeast leader peptide sequence and its associated yeast-recognized processing site when present.

For purposes of the present invention, SP is a presequence that is an N-terminal sequence for the precursor polypeptide of the mature form of a yeast secreted protein. When the nucleotide sequence encoding the hybrid precursor polypeptide is expressed in a transformed yeast host cell, the signal peptide sequence functions to direct the hybrid precursor polypeptide comprising the mature heterologous protein of interest into the endoplasmic reticulum (ER). Movement into the lumen of the ER represents the initial step into the secretory pathway of the yeast host cell. Although the signal peptide of the invention can be heterologous to the yeast host cell, more preferably the signal peptide will be native to the host cell.

The signal peptide sequence of the invention may be a known naturally occurring signal sequence or any variant thereof as described above that does not adversely affect the function of the signal peptide. Examples of signal peptides appropriate for the present invention include, but are not limited to, the signal peptide sequences for α-factor (see, for example, U.S. Pat. No. 5,602,034; Brake et al. (1984) *Proc. Natl. Acad. Sci. USA* 81:4642–4646); invertase (WO 84/01153); PHO5 (DK 3614/83); YAP3 (yeast aspartic protease 3; PCT Publication No. 95/02059); and BAR1 (PCT Publication No. 87/02670). Alternatively, the signal peptide sequence may be determined from genomic or cDNA libraries using hybridization probe techniques available in the art (see Sambrook et al. (1989) *Molecular Cloning: A Laboratory Manual* (Cold Spring Harbor Laboratory Press, Plainview, N.Y.), or even synthetically derived (see, for example, WO 92/11378).

During entry into the ER, the signal peptide is cleaved off the precursor polypeptide at a processing site. The processing site can comprise any peptide sequence that is recognized in vivo by a yeast proteolytic enzyme. This processing site may be the naturally occurring processing site for the signal peptide. More preferably, the naturally occurring processing site will be modified, or the processing site will be synthetically derived, so as to be a preferred processing site. By "preferred processing site" is intended a processing site that is cleaved in vivo by a yeast proteolytic enzyme more efficiently than is the naturally occurring site. Examples of preferred processing sites include, but are not limited to, dibasic peptides, particularly any combination of the two basic residues Lys and Arg, that is Lys-Lys, Lys-Arg, Arg-Lys, or Arg-Arg, most preferably Lys-Arg. These sites are cleaved by the endopeptidase encoded by the KEX2 gene of *Saccharomyces cerevisiae* (see Fuller et al. *Microbiology* 1986:273–278) or the equivalent protease of other yeast species (see Julius et al. (1983) *Cell* 32:839–852). In the event that the KEX2 endopeptidase would cleave a site within the peptide sequence for the mature heterologous protein of interest, other preferred processing sites could be utilized such that the peptide sequence of interest remains intact (see, for example, Sambrook et al. (1989) *Molecular Cloning: A Laboratory Manual* (Cold Spring Harbor Laboratory Press, Plainview, N.Y.).

A functional signal peptide sequence is essential to bring about extracellular secretion of a heterologous protein from a yeast cell. Additionally, the hybrid precursor polypeptide may comprise a secretion leader peptide sequence of a yeast secreted protein to further facilitate this secretion process. When present, the leader peptide sequence is generally positioned immediately 3' to the signal peptide sequence processing site. By "secretion leader peptide sequence" (LP) is intended a peptide that directs movement of a precursor polypeptide, which for the purposes of this invention is the hybrid precursor polypeptide comprising the mature heterologous protein to be secreted, from the ER to the Golgi apparatus and from there to a secretory vesicle for secretion across the cell membrane into the cell wall area and/or the growth medium. The leader peptide sequence may be native or heterologous to the yeast host cell but more preferably is native to the host cell.

The leader peptide sequence of the present invention may be a naturally occurring sequence for the same yeast secreted protein that served as the source of the signal peptide sequence, a naturally occurring sequence for a different yeast secreted protein, or a synthetic sequence (see, for example, WO 92/11378), or any variants thereof that do not adversely affect the function of the leader peptide.

For purposes of the invention, the leader peptide sequence when present is preferably derived from the same yeast secreted protein that served as the source of the signal peptide sequence, more preferably an α-factor protein. A number of genes encoding precursor α-factor proteins have been cloned and their combined signal-leader peptide sequences identified. See, for example, Singh et al. (1983) *Nucleic Acids Res.* 11:4049–4063; Kurjan et al., U.S. Pat. Nos. 4,546,082; 5,010,182; herein incorporated by reference. Alpha-factor signal-leader peptide sequences have been used to express heterologous proteins in yeast. See, for example, Elliott et al. (1983) *Proc. Natl. Acad. Sci. USA* 80:7080–7084; Bitter et al. (1984) *Proc. Natl. Acad. Sci.* 81:5330–5334; Smith et al. (1985) *Science* 229:1219–1229; and U.S. Pat. Nos. 4,849,407 and 5,219,759; herein incorporated by reference.

Alpha-factor, an oligopeptide mating pheromone approximately 13 residues in length, is produced from a larger precursor polypeptide of between about 100 and 200 residues in length, more typically about 120–160 residues. This precursor polypeptide comprises the signal sequence, which is about 19–23 (more typically 20–22 residues), the leader sequence, which is about 60 residues, and typically 2–6 tandem repeats of the mature pheromone sequence. Although the signal peptide sequence and full-length α-factor leader peptide sequence can be used, more preferably for this invention a truncated α-factor leader peptide sequence will be used with the signal peptide when both elements are present in the hybrid precursor molecule.

By "truncated" α-factor leader peptide sequence is intended a portion of the full-length α-factor leader peptide sequence that is about 20 to about 60 amino acid residues, preferably about 25 to about 50 residues, more preferably about 30 to about 40 residues in length. Methods for using truncated α-factor leader sequences to direct secretion of heterologous proteins in yeast are known in the art. See particularly U.S. Pat. No. 5,602,034. When the hybrid precursor polypeptide sequence comprises a truncated α-factor leader peptide, deletions to the full-length leader will preferably be from the C-terminal end and will be done in such a way as to retain at least one glycosylation site (-Asn-Y-Thr/Ser-, where Y is any amino acid residue) in the truncated peptide sequence. This glycosylation site, whose modification is within skill in the art, is retained to facilitate secretion (see particularly WO 89/02463).

When the hybrid precursor polypeptide sequence of the present invention comprises a leader peptide sequence, such as the α-factor leader sequence, there will be a processing site immediately adjacent to the 3' end of the leader peptide sequence. This processing site enables a proteolytic enzyme native to the yeast host cell to cleave the yeast secretion leader peptide sequence from the 5' end of the native N-terminal propeptide sequence of the mature heterologous protein of interest, when present, or from the 5' end of the peptide sequence for the mature heterologous protein of interest. The processing site can comprise any peptide sequence that is recognized in vivo by a yeast proteolytic enzyme such that the mature heterologous protein of interest can be processed correctly. The peptide sequence for this processing site may be a naturally occurring peptide sequence for the native processing site of the leader peptide sequence. More preferably, the naturally occurring processing site will be modified, or the processing site will be synthetically derived, so as to be a preferred processing site as described above.

In the present invention, the nucleotide sequence encoding the hybrid precursor polypeptide comprises a native propeptide sequence ($PRO_{MHP}$) for the mature heterologous protein of interest. By "native propeptide sequence" or "native prosequence" is intended that portion of an intermediate precursor polypeptide (which is called a "pro-protein") for a mature secreted protein that remains attached to the N-terminal and/or C-terminal end of the mature protein sequence following cleavage of the native signal peptide sequence (or presequence) from the initial precursor polypeptide (or "prepro-protein"). The residues of the propeptide sequence are not contained in the mature secreted protein. Rather, such extra residues are removed at processing sites by proteolytic enzymes near the end of the secretory pathway, in the trans-Golgi network (Griffiths and Simons (1986) *Science* 234:438–443) and secretory granules (Orci et al. (1986) *J. Cell Biol.* 103:2273–2281).

The present invention provides for the presence of propeptide sequences that naturally occur at the N-terminal and/or C-terminal end of the native pro-protein precursor form of the mature heterologous protein of interest. Thus, a propeptide sequence may be positioned between the 3' end of the signal peptide sequence processing site, or the 3' end of the yeast-recognized processing site adjacent to the leader peptide sequence if present, and the 5' end of the peptide sequence for the mature heterologous protein of interest (an N-terminal propeptide sequence, PROMHP) or immediately adjacent to the 3' end of the peptide sequence for the mature heterologous protein of interest (a C-terminal propeptide sequence, $CPRO_{MHP}$), depending on its orientation within the native pro-protein. The invention also provides for inclusion of both an N-terminal and a C-terminal propeptide sequence flanking the peptide sequence for the mature heterologous protein of interest when both propeptide sequences exist in the native pro-protein. Where both an N-terminal and a C-terminal propeptide sequence exists in the native pro-protein, preference for inclusion of both propeptide sequences in the hybrid precursor polypeptide will be experimentally determined.

Methods are available in the art for determining the naturally occurring processing sites for the native signal peptide and propeptide sequences of a prepro-protein (see, for example, von Heijne (1983) *Eur. J. Biochem.* 133:17–21, (1984) *J. Mol. Biol.* 173: 243–251, (1986) *J. Mol. Biol.* 184:99–105, and (1986) *Nucleic Acids Res.* 14:4683–4690) such that the native N-terminal and/or C-terminal propeptide sequence can be determined for use in the invention.

Immediately 3' to the native N-terminal propeptide sequence (when present) or immediately 5' to the C-terminal propeptide sequence (when present) is a processing site that is recognized in vivo by a yeast proteolytic enzyme. This processing site allows for cleavage of the propeptide sequence from the peptide sequence for the mature heterologous protein of interest (MHP). It is recognized that this processing site may be the naturally occurring processing site for the propeptide sequence if the naturally occurring site is recognized in vivo by a proteolytic enzyme of the yeast host cell. More preferably, the naturally occurring processing site will be modified, or the processing site will be synthetically derived, so as to be a preferred processing site. Examples of preferred processing sites include, but are not limited to, those discussed above for the other processing. Preferably all of these processing sites will be similar such that the same yeast proteolytic enzyme brings about cleavage of the signal and leader peptide sequences and the native propeptide sequence(s).

In accordance with the invention as stated above, the yeast signal peptide and secretion leader peptide sequences, as well as the native propeptide sequences, represent those parts of the hybrid precursor polypeptide of the invention that can direct the sequence for the mature heterologous protein of interest through the secretory pathway of a yeast host cell.

In one preferred embodiment of the present invention, the nucleotide sequence of the hybrid precursor polypeptide comprises in the 5' to 3' direction:

$$5\text{-AFSP-tAFLP-PS}_L\text{-NPRO}_{PDGF}\text{-PS}_{NPRO}\text{-M}_{PDGF}\text{-3'}$$

wherein:
AFSP comprises an α-factor signal peptide sequence and a processing site;
tAFLP comprises a truncated α-factor secretion leader peptide sequence;
$PS_L$ comprises a preferred processing site for the leader peptide sequence;
$NPRO_{PDGF}$ comprises the peptide sequence for a native N-terminal propeptide of a mature platelet-derived growth factor (PDGF);
$PS_{NPRO}$ comprises a preferred processing site for the N-terminal propeptide sequence; and
$M_{PDGF}$ comprises the sequence for said mature PDGF.

Preferably the α-factor signal peptide and truncated α-factor secretion leader peptide sequences are derived from the Matα gene of *S. cerevisiae* as outlined in the examples. The preferred truncated α-factor leader peptide sequence will include the N-terminal portion of the full-length leader sequence; that is, the leader sequence will start with the first amino acid residue of the full-length sequence and run the length of about 20 to about 60 amino acid residues, preferably about 25 to about 50 residues, more preferably about 30 to about 40 residues. In one embodiment, a leader of about 35 residues is used.

The mature protein of this preferred embodiment is human platelet-derived growth factor (PDGF). PDGF, the primary mitogen in serum for mesenchymal-derived cells, is stored in platelet alpha-granules. Injury to blood vessels activates the release of PDGF from these granules in the vicinity of the injured vessels. This mitogen acts as a potent chemoattractant for fibroblasts and smooth muscle cells, as well as monocytes and neutrophils. The mitogenic activity of the localized PDGF results in proliferation of these cells at the site of injury, contributing to the process of wound repair.

Purified native platelet-derived growth factor (PDGF), a glycoprotein of about 30,000 daltons, is composed of two disulfide-linked polypeptide chains. Two forms of these chains, designated A and B, have been identified. The native protein occurs as the homodimer AA or BB or the heterodimer AB, or a mixture thereof. A partial amino acid sequence for the PDGF-A chain has been identified (Johnsson et al. (1984) *EMBO J.* 3:921–928) and cDNAs encoding two forms of PDGF A-chain precursors have been described (U.S. Pat. No. 5,219,759). The A-chain is derived by proteolytic processing of a 211 amino acid precursor polypeptide. The cDNA encoding the PDGF-B chain has also been described (*Nature* (1985) 316:748–750). The B-chain is derived byproteolytic processing of a 241 amino acid precursor.

The mature PDGF protein of the present invention will be the biologically active dimeric form, including the homodimers PDGF-AA and PDGF-BB or the heterodimer PDGF-AB, and any substantially homologous and functionally equivalent variants thereof as defined above. For example, the native amino acid sequence for the A-chain or the B-chain may be truncated at either the N-terminal or C-terminal end. Thus removal of up to 15 or up to 10 amino acids from the N-terminal or C-terminal end, respectively, of the B-chain does not affect biological activity of the variant. Additionally, amino-acid substitutions may be made. For example, an amino acid such as serine may be substituted for any of the cysteine residues at positions 43, 52, 53, and 97 of the native human B-chain and at corresponding positions in the native A-chain to obtain substantially homologous and functionally equivalent variants of the native chain. Variants of the A-chain are known based on cloned DNA sequences, such as, for example, variants having an additional 6 or 19 amino acids at the C-terminal end. See, for example, Tong et al. (1987) *Nature* 328:619–621; Betsholtz et al. (1986) *Nature* 320:695–699. One PDGF B-chain variant may be the corresponding substantially homologous portion of the amino-acid sequence encoded by the v-sis gene of simian sarcoma virus. The homologous region of the product of this gene, $p28^{sis}$, begins at amino acid 67 and continues to amino acid 175, and differs from the human B-chain by only 4 amino acid residues (see, for example, European Patent Application No. 0 487 116 A1). Functionally equivalent variants can be determined with assays for biological activity as described in the examples.

The nucleotide sequence encoding the mature PDGF protein of the present invention may be genomic, cDNA, or synthetic DNA. The genes encoding the native forms of PDGF have been sequenced, and several variants are well known in the art. Expression of PDGF homodimers and heterodimers is described in, for example, U.S. Pat. Nos. 4,766,073; 4,769,328; 4,801,542; 4,845,075; 4,849,407; 5,045,633; 5,128,321; and 5,187,263; herein incorporated by reference. Based on the known amino acid sequences for the A- and B-chain polypeptides, synthetic nucleotide sequences encoding PDGF A-chain and B-chain polypeptides may be made in vitro using methods available in the art. See particularly Sambrook et al. (1989) *Molecular Cloning: A Laboratory Manual* (Cold Spring Harbor Laboratory Press, Plainview, N.Y.). Where the mature protein of interest is the heterodimer PDGF-AB, the nucleotide sequences encoding the hybrid precursor polypeptides comprising the A- and B-chain polypeptides may be assembled as part of one expression cassette or assembled into separate expression cassettes for cotransformation of a yeast host cell.

In this preferred embodiment comprising mature PDGF, the C-terminal end of the truncated α-factor secretion leader peptide sequence and of the native N-terminal propeptide sequence will terminate in a preferred processing site, preferably a dibasic processing site that is specific for the KEX2 endopeptidase of *S. cerevisiae*. The dipeptides can be any combination of the basic residues Lys and Arg, more preferably a Lys-Arg dipeptide.

The native prepro-PDGF-B additionally comprises a 51 amino acid C-terminal propeptide. In another preferred embodiment, the nucleotide sequence encoding the hybrid precursor polypeptide comprises in the 5' to 3' direction the following modified sequence:

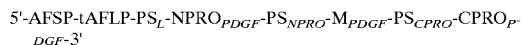
5'-AFSP-tAFLP-PS$_L$-NPRO$_{PDGF}$-PS$_{NPRO}$-M$_{PDGF}$-PS$_{CPRO}$-CPRO$_{PDGF}$-3' wherein:

CPRO$_{PDGF}$ comprises a C-terminal propeptide sequence for said PDGF mature heterologous protein of interest; and PS$_{CPRO}$ comprises a preferred processing site for the C-terminal propeptide sequence.

Preferably the preferred processing site for the C-terminal propeptide sequence is similar to that of the leader peptide sequence and the N-terminal propeptide sequence, such that the same yeast proteolytic enzyme brings about cleavage of the α-factor leader peptide sequence and the sequences for both of the native propeptides. Inclusion of these two additional components is experimentally determined.

In another preferred embodiment of the invention, the nucleotide sequence of the hybrid precursor polypeptide comprises in the 5' to 3' direction:

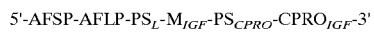
5'-AFSP-AFLP-PS$_L$-M$_{IGF}$-PS$_{CPRO}$-CPRO$_{IGF}$-3' wherein:

AFSP comprises an α-factor signal peptide sequence and a processing site;

AFLP comprises an α-factor secretion leader peptide sequence

PS$_L$ comprises a preferred processing site for the leader peptide sequence;

M$_{IGF}$ comprises the peptide sequence for a mature insulin-like growth factor (IGF);

PS$_{CPRO}$ comprises a preferred processing site for the C-terminal propeptide sequence; and CPRO$_{IGF}$ comprises the peptide sequence for a native C-terminal propeptide of said mature IGF.

Preferably the α-factor signal peptide and α-factor secretion leader peptide sequences are derived from the Matα gene of *S. cerevisiae* as outlined for the preferred embodiment for PDGF.

The mature protein of this preferred embodiment is insulin-like growth factor (IGF), more particularly IGF-I. Insulin-like growth factor (IGF-I) belongs to a family of polypeptides known as somatomedins. IGF-I stimulates growth and division of a variety of cell types, particularly during development. See, for example, European Patent Application Nos. 560,723 A and 436,469 B. Thus, processes such as skeletal growth and cell replication are affected by IGF-I levels.

IGF-I is structurally and functionally similar to, but antigenically distinct from, insulin. In this regard, IGF-I is a single-chain polypeptide with three intrachain disulfide bridges and four domains known as the A, B, C, and D domains, respectively. The A and B domains are connected by the C domain, and are homologous to the corresponding domains of proinsulin. The D domain, a C-terminal prosequence, is present in IGF-I but is absent from proinsulin. IGF-I has 70 amino acid residues and a molecular mass of approximately 7.5 kDa. See Rinderknecht (1978) *J. Biol. Chem.*253:2769 and *FEBS Lett.* 89:283. For a review of IGF, see Humbel (1990) *Eur. J. Biochem.* 190:445–462.

The mature IGF protein of the present invention will be the biologically active form and any substantially homologous and functionally equivalent variants thereof as defined above. Functionally equivalent variants can be determined with assays for biological activity, including the assay, as described in the examples. Representative assays include known radioreceptor assays using placental membranes (see, for example, U.S. Pat. No. 5,324,639; Hall et al. (1974) *J. Clin. Endocrinol. and Metab.* 39:973–976; and Marshall et al. (1974) *J. Clin. Endocrinol. and Metab.* 39:283–292), a bioassay that measures the ability of the molecule to enhance incorporation of tritiated thymidine, in a dose-dependent manner, into the DNA of BALB/c 3T3 fibroblasts (see, for example, Tamura et al. (1989) *J. Biol. Chem.* 262:5616–5621), and the like; herein incorporated by reference.

The art provides substantial guidance regarding the preparation and use of IGF-I variants. For example, fragment of IGF-I will generally include at least about 10 contiguous amino acid residues of the full-length molecule, preferably about 15–25 contiguous amino acid residues of the full-length molecule, and most preferably about 20–50 or more contiguous amino acid residues of full-length IGF-I. The term "IGF-I analog" also captures peptides having one or more peptide mimics ("peptoids"), such as those described in International Publication No. WO 91/04282. Several IGF-I analogs and fragments are known in the art and include those described in, for example, *Proc. Natl. Acad. Sci. USA* (1986) 83:4904–4907; *Biochem. Biophys. Res. Commun.* (1987) 149:398–404; *J. Biol. Chem.* (1988) 263:6233–6239; *Biochem. Biophys. Res. Commun.* (1989) 165:766–771; Forsberg et al. (1990) *Biochem. J.* 271:357–363; U.S. Pat. Nos. 4,876,242 and 5,077,276; International Publication No. WO 87/01038 and WO 89/05822; herein incorporated by reference. Representative analogs include one with a deletion of Glu-3 of the mature molecule, analogs with up to five amino acids truncated from the N-terminus, an analog with a tuncation of the first three N-terminal amino acids and an analog including the first 17 amino acids of the B chain of human insulin in place of the first 16 amino acids of human IGF-1.

The nucleotide sequence encoding the mature IGF protein of the present invention may be genomic, cDNA, or synthetic DNA. The genes encoding the native forms of IGF have been sequenced, and several variants are well known in the art. IGF-I and variants thereof can be produced in any number of ways that are well known in the art. For example, the IGF-I polypeptides can be isolated directly from blood, such as from serum or plasma, by known methods. See, for example, U.S. Pat. No. 4,769,361; Svoboda et al. (1980) *Biochemistry* 19:790–797; Cornell and Boughdady (1982) *Prep. Biochem.* 12:57 and (1984) *Prep. Biochem.* 14:123; herein incorporated by reference. Alternatively, IGF-I can be synthesized chemically, by any of several techniques that are known to those skilled in the art. See, for example, Stewart and Young (1984) *Solid Phase Peptide Synthesis* (Pierce Chemical Company, Rockford, Ill.) and Barany and Merrifield (1980) *The Peptides: Analysis, Synthesis, Biology* (eds. Gross and Meienhofer) pp. 3–254, Vol. 2 (Academic Press, New York), for solid phase peptide synthesis techniques; and Bodansky (1984) *Principles of Peptide Synthesis* (Springer-Verlag, Berlin) and Gross and Meienhofer, eds. (1980) *The Peptides: Analysis, Synthesis, Biology*, Vol. 1, for classical solution synthesis; herein incorporated by reference. The IGF-I polypeptides of the present invention can also be chemically prepared by the method of simultaneous multiple peptide synthesis. See, for example, Houghten (1985) *Proc. Natl. Acad. Sci. USA* 82:5131–5135; U.S. Pat. No. 4,631, 211; herein incorporated by reference.

In this preferred embodiment comprising mature IGF-I, the C-terminal end of the truncated α-factor secretion leader peptide sequence and the N-terminal end of the native C-terminal propeptide sequence will terminate in a preferred processing site, preferably a dibasic processing site that is specific for the KEX2 endopeptidase of *S. cerevisiae*. The dipeptides can be any combination of the basic residues Lys and Arg, more preferably a Lys-Arg dipeptide.

The nucleotide sequences of the present invention are useful for producing biologically active mature heterologous proteins of interest in a yeast host cell when operably linked to a yeast promoter. In this manner, the nucleotide sequences encoding the hybrid precursor polypeptides of the invention are provided in expression cassettes for introduction into a yeast host cell. These expression cassettes will comprise a transcriptional initiation region linked to the nucleotide sequence encoding the hybrid precursor polypeptide. Such an expression cassette is provided with a plurality of restriction sites for insertion of the nucleotide sequence to be under the transcriptional regulation of the regulatory regions. The expression cassette may additionally contain selectable marker genes.

Such an expression cassette comprises in the 5' to 3' direction and operably linked a yeast-recognized transcription and translation initiation region, a nucleotide coding sequence for the hybrid precursor polypeptide comprising the sequence for the mature protein of interest, and a yeast-recognized transcription and translation termination region. By "operably linked" is intended expression of the coding sequence for the hybrid precursor polypeptide is under the regulatory control of the yeast-recognized transcription and translation initiation and termination regions.

By "yeast-recognized transcription and translation initiation and termination regions" is intended regulatory regions that flank a coding sequence, in this case the nucleotide sequence encoding the hybrid polypeptide sequence, and control transcription and translation of the coding sequence in a yeast. These regulatory regions must be functional in the yeast host. The transcription initiation region, the yeast promoter, provides a binding site for RNA polymerase to initiate downstream (3') translation of the coding sequence. The promoter may be a constitutive or inducible promoter, and may be native or analogous or foreign or heterologous to the specific yeast host. Additionally, the promoter may be the natural sequence or alternatively a synthetic sequence. By foreign is intended that the transcription initiation region is not found in the native yeast of interest into which the transcription initiation region is introduced.

Suitable native yeast promoters include, but are not limited to the wild-type α-factor promoter, as well as other yeast promoters. Preferably the promoter is selected from the list including promoters for the glycolytic enzymes phosphoglucoisomerase, phosphofructokinase, phosphotrioseisomerase, phosphoglucomutase, enolase, pyruvate kinase (PyK), glyceraldehyde-3-phosphate dehydrogenase (GAP or GAPDH), alcohol dehydrogenase (ADH) (EPO Publication No. 284,044). See, for example, EPO Publication Nos. 120,551 and 164,556.

Synthetic hybrid promoters consisting of the upstream activator sequence of one yeast promoter, which allows for inducible expression, and the transcription activation region of another yeast promoter also serve as functional promoters in a yeast host. Examples of hybrid promoters include ADH/GAP, where the inducible region of the ADH promoter is combined with the activation region of the GAP promoter (U.S. Pat. Nos. 4,876,197 and 4,880,734). Other hybrid promoters using upstream activator sequences of either the ADH2, GAL4, GAL10, or PHO5 genes combined with the transcriptional activation region of a glycolytic enzyme such as GAP or PyK are available in the art (EPO Publication No. 164,556). More preferably the yeast promoter is the inducible ADH/GAP hybrid promoter.

Yeast-recognized promoters also include naturally occurring non-yeast promoters that bind yeast RNA polymerase and initiate translation of the coding sequence. Such promoters are available in the art. See, for example, Cohen et al. (1980) *Proc. Natl. Acad. Sci. USA* 77:1078; Mercereau-Puigalon et al. (1980) *Gene* 11:163; Panthier et al. (1980) *Curr. Genet.* 2:109); Henikoff et al. (1981) *Nature* 283:835; and Hollenberg et al. (1981) *Curr. Topics Microbiol. Immunol.* 96:119; herein incorporated by reference.

The termination regulatory region of the expression cassette may be native with the transcription initiation region, or may be derived from another source, providing that it is recognized by the yeast host. The termination regions may be those of the native α-factor transcription termination sequence, or another yeast-recognized termination sequence, such as those for the glycolytic enzymes mentioned above. More preferably the transcription terminator is the Matα (α-factor) transcription terminator described in U.S. Pat. No. 4,870,008.

The nucleotide sequences encoding the hybrid precursor polypeptides of the invention are provided in expression cassettes for expression in a yeast host. The cassette will include 5' and 3' regulatory sequences operably linked to the nucleotide sequence encoding the hybrid precursor polypeptide of interest. The cassette may also contain at least one additional nucleotide sequence of interest to be cotransformed into the yeast host. Alternatively, the additional nucleotide sequences can be provided on another expression cassette. Where appropriate, the nucleotide sequence encoding the hybrid precursor polypeptide and any additional nucleotide sequences of interest may be optimized for increased expression in the transformed yeast. That is, these nucleotide sequences can be synthesized using yeast-preferred codons for improved expression. Methods are available in the art for synthesizing yeast-preferred nucleotide sequences of interest (see, for example, U.S. Pat. Nos. 5,219,759 and 5,602,034).

Additional sequence modifications are known to enhance expression of nucleotide coding sequences in a cellular host. These include elimination of sequences encoding spurious polyadenylation signals, exon-intron splice site signals, transposon-like repeats, and other such well-characterized sequences that may be deleterious to gene expression. The G-C content of the sequence maybe adjusted to levels average for a given cellular host, as calculated by reference to known genes expressed in the host cell. When possible, the nucleotide coding sequence is modified to avoid predicted hairpin secondary mRNA structures.

In preparing the expression cassette, the various nucleotide sequence fragments may be manipulated, so as to provide for the sequences in the proper orientation and, as appropriate, in the proper reading frame. Toward this end, adapters or linkers may be employed to join the nucleotide fragments or other manipulations may be involved to provide for convenient restriction sites, removal of superfluous nucleotides, removal of restriction sites, or the like. For this purpose, in vitro mutagenesis, primer repair, restriction, annealing, resubstitutions, e.g., transitions and transversions, may be involved. See particularly Sambrook et al. (1989) *Molecular Cloning: A Laboratory Manual* (Cold Spring Harbor Laboratory Press, Plainview, N.Y.).

The expression cassettes of the present invention can be ligated into a replicon (e.g., plasmid, cosmid, virus, minichromosome), thus forming an expression vector that is capable of autonomous DNA replication in vivo. Preferably the replicon will be a plasmid. Such a plasmid expression vector will be maintained in one or more replication systems, preferably two replications systems, that allow for stable maintenance within a yeast host cell for expression purposes, and within a prokaryotic host for cloning purposes. Examples of such yeast-bacteria shuttle vectors include Yep24 (Botstein et al. (1979) *Gene* 8:17–24; pC1/1 (Brake et al. (1984) *Proc. Natl. Acad. Sci. USA* 81:4642–4646), and Yrp17 (Stnichomb et al. (1982) *J. Mol. Biol.* 158:157).

Additionally, a plasmid expression vector may be a high or low copy number plasmid, the copy number generally ranging from about 1 to about 200. With high copy number yeast vectors, there will generally be at least 10, preferably at least 20, and usually not exceeding about 150 copies in a single host. Depending upon the heterologous protein selected, either a high or low copy number vector may be desirable, depending upon the effect of the vector and the foreign protein on the host. See, for example, Brake et al. (1984) *Proc. Natl. Acad. Sci. USA* 81:4642–4646. DNA constructs of the present invention can also be integrated into the yeast genome by an integrating vector. Examples of such vectors are known in the art. See, for example, Botstein et al. (1979) *Gene* 8:17–24.

The host chosen for expression of the heterologous proteins of the invention will preferably be a yeast. By "yeast" is intended ascosporogenous yeasts (Endomycetales), asidiosporogenous yeasts, and yeast belonging to the Fungi Imperfecti (Blastomycetes). The ascosporogenous yeasts are divided into two families, Spermophthoraceae and Saccharomycetaceae. The later is comprised of four subfamilies, Schizosaccharomycoideae (e.g., genus Schizosaccharomyces), Nadsonioideae, Lipomycoideae, and Saccharomycoideae (e.g., genera Pichia, Kluyveromyces, and Saccharomyces). The basidiosporogenous yeasts include the genera Leucosporidium, Rhodosporidium, Sporidiobolus, Filobasidium, and Filobasidiella. Yeast belonging to the Fungi Imperfecti are divided into two families, Sporobolomycetaceae (e.g., genera Sporobolomyces, Bullera) and Cryptococcaceae (e.g., genus Candida). Of particular interest to the present invention are species within the genera Pichia, Kluyveromyces, Saccharomyces, Schizosaccharomyces, and Candida. Of particular interest are the Saccharomyces species *S. cerevisiae, S. carlsbergensis, S. diastaticus, S. douglasi, S. kluyveri, S. norbensis,* and *S. oviformis*. Species of particular interest in the genus Kluyveromyces include *K. lactis*. Since the classification of yeast may change in the future, for the purposes of this invention, yeast shall be defined as described in Skinner et al., eds. 1980) *Biology andactivities of Yeast* (Soc. App. Bacteriol. Symp. Series No. 9). In addition to the foregoing, those of ordinary skill in the art are presumably familiar with the biology of yeast and the manipulation of yeast genetics. See, for example, Bacila et al., eds. (1978) *Biochemistry and Genetics of Yeast;* Rose and Harrison, eds. (1987) *The Yeasts* (2$^{nd}$ ed.); Strathem et al., eds. (1981) *The Molecular Biology of the Yeast Saccharomyces;* herein incorporated by reference.

The selection of suitable yeast and other microorganism hosts for the practice of the present invention is within the skill of the art. When selecting yeast hosts for expression, suitable hosts may include those shown to have, inter alia, good secretion capacity, low proteolytic activity, and overall vigor. Yeast and other microorganisms are generally available from a variety of sources, including the Yeast Genetic Stock Center, Department of Biophysics and Medical Physics, University of California, Berkeley, Calif.; and the American Type Culture Collection, Rockville, Md.

Methods of introducing exogenous DNA into yeast hosts are well known in the art. There is a wide variety of ways to transform yeast. For example, spheroplast transformation is taught by Hinnen et al. (1978) *Proc. Natl. Acad. Sci. USA* 75:1919–1933 and Stinchcomb et al., EPO Publication No. 45,573; herein incorporated by reference. Transformants are grown in an appropriate nutrient medium, and, where appropriate, maintained under selective pressure to insure retention of endogenous DNA. Where expression is inducible, growth can be permitted of the yeast host to yield a high density of cells, and then expression is induced. The secreted, mature heterologous protein can be harvested by any conventional means, and purified by chromatography, electrophoresis, dialysis, solvent-solvent extraction, and the like.

The following examples are offered by way of illustration and not by way of limitation.

EXPERIMENTAL

The following examples further describe the construction of an expression vector comprising the nucleotide sequence encoding mature human PDGF-B in accordance with the disclosed invention. Examples demonstrating the use of this expression vector to produce biologically active mature PDGF-BB in a yeast host are also provided.

Additional examples describe an expression vector comprising the nucleotide sequence encoding mature human IGF-I in accordance with the disclosed invention and demonstrate the use of this expression vector to produce biologically active mature IGF-I in a yeast host.

Example 1

Plasmid Vector pAB24

The vector selected for expressing rhPDGF-BB, pAB24, is a yeast-bacteria shuttle vector. The plasmid is a chimera of sequences from pBR322, derived from several naturally occurring bacterial plasmids, and sequences of the endogenous *S. cerevisiae* 2-$\mu$ plasmid (Broach (1981) in *Molecular Biology of the Yeast Saccharomyces* (Cold Spring Harbor Press, New York), 1:445–470). It also encodes genes enabling selection in both *E. coli* and *S. cerevisiae* hosts. The pBR322 part of pAB24 includes the ampicillin resistance (Ap$^r$)-conferring gene encoding β-lactamase, as well as a gene conferring tetracycline resistance (Tc$^r$). These genes allow transformation of competent *E. coli* and selection of plasmid-containing bacteria. A unique BamHI cloning site, present in the gene encoding tetracycline resistance, is the site utilized for insertion of an expression cassette. The pBR322 portion of the vector also includes a ColE1-like replication origin enabling replication in *E. coli*. Two *S. cerevisiae* genes derived from YEp24 (Botstein et al. (1979) *Gene* 8:17–24), URA3 and leu2d, enable selection in yeast host strains lacking either or both of these genes. The latter gene, leu2d, lacks a portion of the 5'-untranslated promoter region and requires high plasmid copy number for growth in leucine-deficient medium. This is necessary to achieve sufficient LEU2 protein expression for complementation of yeast strains lacking LEU2 (Erhart and Hollenberg (1983) *J. Bacteriol.* 156:625–635). The 2-$\mu$ sequences of pAB24 confer replication and partitioning of the expression plasmid in *S. cerevisiae*. FIG. 1 shows a schematic map of plasmid pAB24 with key restriction sites and genetic elements. A description of the construction of pAB24 can be found in the European Patent Application publication EPO 0324 274 B1.

Three expression plasmids containing the PDGF-B gene, pYAGL7PB, pYL7PPB (also known as pYAGL7PPB), and PYJST400, were used to produce PDGF-BB in a yeast host. All of these expression vectors utilize pAB24 as the plasmid into which the expression cassette comprising the PDGF-B gene was inserted.

Example 2

Construction of Expression Plasmid pYAGL7PB

General Description

Plasmid pYAGL7PB includes an expression cassette with the following features. Transcription is mediated by the inducible, hybrid yeast promoter ADH/GAP. This promoter includes ADR2 transcription factor responsive sequences from the *S. cerevisiae* ADH2 gene (Beier and Young (1982) *Nature* 300:724–728) and promoter sequences from the *S. cerevisiae* gene TDH3, encoding the glycolytic enzyme glyceraldehyde-3-phosphate dehydrogenase (GAP). The ADR2 transcription factor responsive sequences confer inducible gene transcription upon downstream sequences. Induction is achieved by glucose depletion in the growth medium. Termination of transcription is mediated by the terminator derived from the *S. cerevisiae* mating factor type alpha (Matα) gene (Brake et al. (1984) *Proc. Natl. Acad. Sci. USA* 81:4642–4646).

Figure 2:
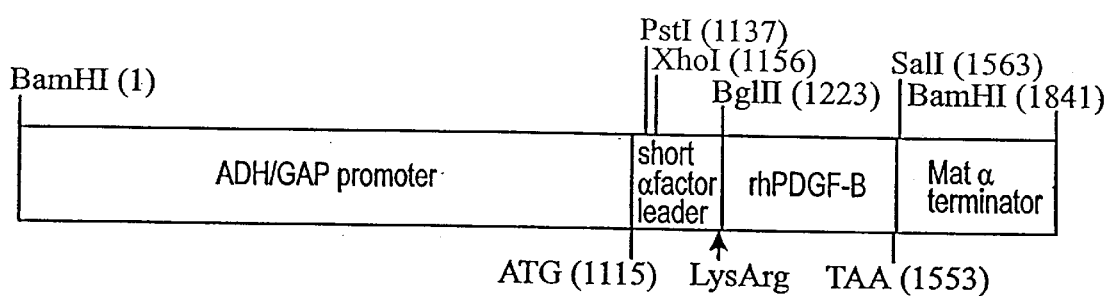
FIG. 2 is a map of the rhPDGF-B expression cassette in pAGL7PB and pYAGL7PB.

The cassette further includes an open reading frame encoding a truncated Matα sequence fused to a sequence encoding the human PDGF-B gene. The truncated α-factor leader mediates secretion of in-frame protein fusions. It is a derivative of *S. cerevisiae* α-factor leader, the product of the Matα gene (Kurjan and Herskowitz (1982) *Cell* 30:933–943). A dibasic amino acid processing site is present at the truncated α-factor leader/PDGF-B junction to facilitate production of correctly processed rhPDGF-BB polypeptide by yeast. FIG. 2 shows a map of the pYAGL7PB expression cassette highlighting these features and the restriction enzyme sites relevant to the construction of this expression cassette. The nucleotide sequence and predicted amino acid sequence of the open reading frame encoding the truncated α-factor leader-PDGF-B primary translation product are given in SEQ ID NO: 1 and SEQ ID NO: 2, respectively.

Sequential Construction of pYAGL7PB

Following is a description of the sequential steps taken to construct this expression vector.

Construction of PDGF-B Synthetic Gene and Cloning into a Yeast Expression Vector The synthetic gene encoding the partial dibasic processing site and rhPDGF-B (SEQ ID NOs: 3–4) was made from 17 overlapping oligonucleotides (SEQ ID NOs: 5–21) as described in Urdea et. al. (*Proc. Natl. Acad Sci. USA* 80 (1983):7461–7465). Ligation of the fragments results in an XbaI-SalI fragment, which was subsequently inserted into XbaI-SalI cut pPAG/αF vector.

Plasmid pPAG/αF is a pBR322 derivative with an expression cassette delineated by BamHI sites. The expression cassette includes the ADH/GAP hybrid promoter, as well as the open reading frame encoding the yeast α-factor leader (BamHI-XbaI), an XbaI-SalI gene fragment, and the Matα (α-factor) transcription terminator (SalI-BamHI). Substitution of an XbaI-SalI gene fragment (in-frame) capable of heterologous protein expression into this plasmid allows the expression and secretion of the heterologous protein. The isolation of the yeast glyceraldehyde-3-phosphate (GAP) gene promoter, the origin of the ADH2 component of the promoter, and the construction of a hybrid ADH/GAP promoter are described in U.S. Pat. Nos. 4,876,197 and 4,880,734. The isolation of the yeast α-factor gene including the transcription terminator is described in U.S. Pat. No. 4,870,008.

Upon dideoxy sequencing, the synthetic gene sequence was found to have a single base pair mutation, which was repaired by standard procedures. Plasmid pPAGBB-1 is the plasmid derived from pPAG/αF that contains the correct synthetic PDGF-B (XbaI-SalI) gene.

Construction of Synthetic Truncated α-Factor Leader Gene with Dibasic Processing Site The truncated α-factor leader mediates secretion of in-frame hybrid polypeptides. It is a derivative of S. cerevisiae α-factor leader, the secretion leader for mating factor type alpha, the product of the Matα gene (Kurjan and Herskowitz (1982) Cell 30:933–943), and consists of the first 35 amino acids of the native leader. The construction and use of a truncated α-factor leader gene to mediate secretion is described in EPO Publication No. 0324 274 B1. Synthetic oligonucleotides encoding a comparable, partial (amino acids 8–35) truncated α-factor leader (L7) and part of the dibasic processing site were made from oligonucleotides given in SEQ. ID NO: 22 and when assembled with the complementary strand shown in SEQ ID NO: 23 resulted in a PstI-BglII fragment with a 3'-ACGTC- and a 5'-CTAG-overhang to allow for convenient ligation into the expression cassette.

Construction of pAGL7PB

The purpose of this construction was the substitution of the synthetic, partial truncated α-factor leader PstI-BglII gene fragment described above for most of the full-length α-factor leader in the PDGF-B expression cassette of pPAGBB-1. A 1.9 kb Pst I fragment including pBR322 sequences, the ADH/GAP hybrid promoter (marked at the 5' end by a BamHI site) and the 5' partial α-factor leader gene sequence (encoding the first seven amino acids of the native α-factor leader) was isolated from pPAGBB-1. It was ligated to kinased, annealed synthetic oligonucleotides 1.49/3°.40. Following digestion with BamHI, a partial expression cassette 5' fragment was obtained including sequences for the ADH/GAP hybrid promoter and the 5' portion of the truncated α-factor leader.

Similarly, a BglII fragment containing the PDGF-B synthetic gene, the α-factor terminator (marked at the 3' end by a BamHI site) and pBR322 sequences was isolated from pPAGBB-1. It was ligated to kinased, annealed synthetic oligonucleotides 2.32/4°.50. Following digestion with BamHI, a partial expression cassette 3' fragment was obtained including sequences for the 3' portion of the truncated α-factor leader, PDGF-B, and the α-factor leader transcription terminator. The complete PDGF-B expression cassette was obtained following ligation of the 5' and 3' partial expression cassette gene fragments and digestion with BamHI. The BamHI expression cassette was cloned into the BamHI site of a pBR322-derived vector (pBRAEco-Sal) to give plasmid pAGL7PB. A map of the PDGF-B expression cassette in this plasmid is shown in FIG. 2.

Construction of pYAGL7PB

Figure 3:
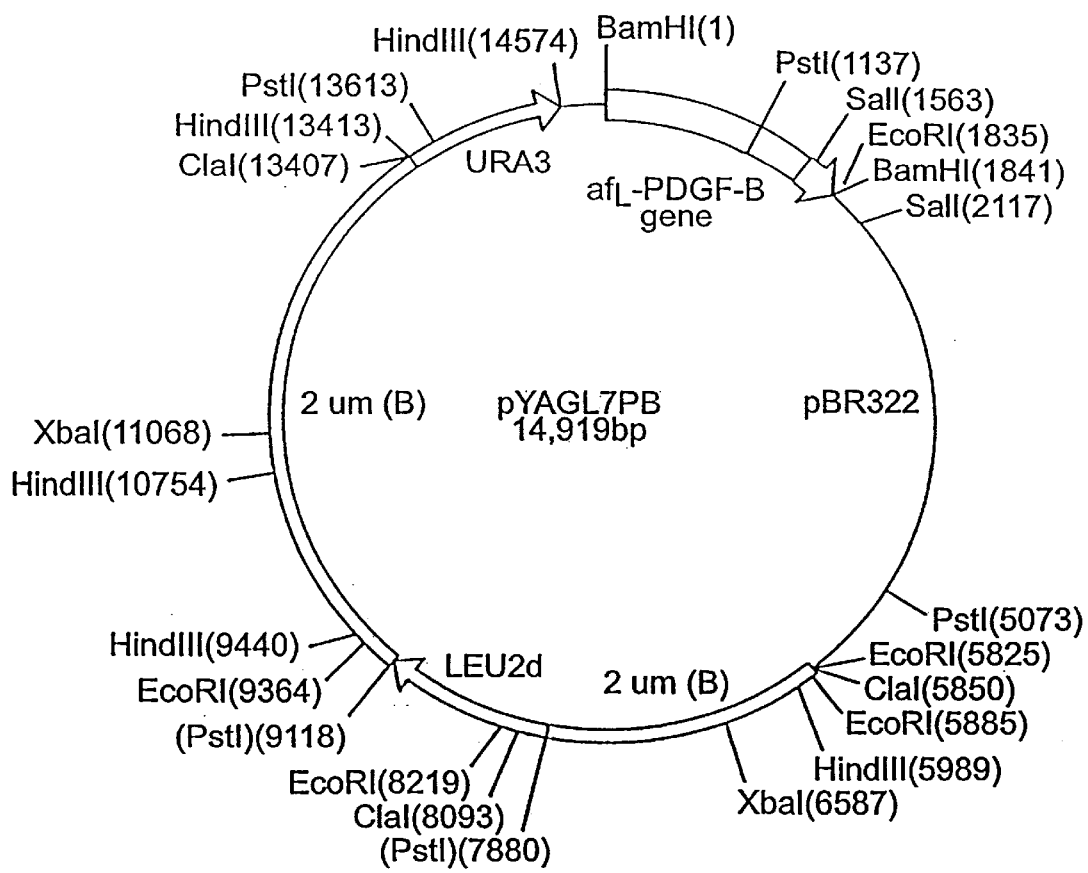
FIG. 3 is a map of rhPDGF-B expression plasmid pYAGL7PB.

The PDGF-B expression cassette of pAGL7PB was isolated by BamHI digestion and inserted into the BamHI site of the yeast-bacteria shuttle vector pAB24 described above. A yeast expression plasmid, pYAGL7PB, was isolated. A plasmid map of pYAGL7PB is shown in FIG. 3. The nucleotide sequence of the complete expression cassette and the predicted amino acid sequence of the open reading frame (ORF) encoding the truncated α-factor leader-PDGF-B primary translation product are given in SEQ ID NO: 24 and SEQ ID NO: 25, respectively.

Expression Strain Identification: MB2-1(pYAGL7PB)

Expression plasmid pYAGL7PB was transformed into S. cerevisiae MB2-1 by standard procedures and prototrophic uracil colonies were selected. Individual colonies from independent transformants were screened for expression following inoculation of single colonies into medium that selects for leucine prototrophs. The medium also is high in glucose to keep expression of sequences under ADR2 regulation (including the PDGF-B gene) repressed. Cultures were subsequently diluted and grown to confluence in low glucose medium lacking uracil. Cell-free culture supernatants were prepared and assayed for PDGF-BB by immunoactivity (ELISA) and by mitogenic activity on 3T3 cells. A high PDGF-BB expressing colony, MB2-1(pYAGL7PB #5), was identified.

Example 3

Construction of Expression Plasmid pYL7PPB

General Description

Figure 4:
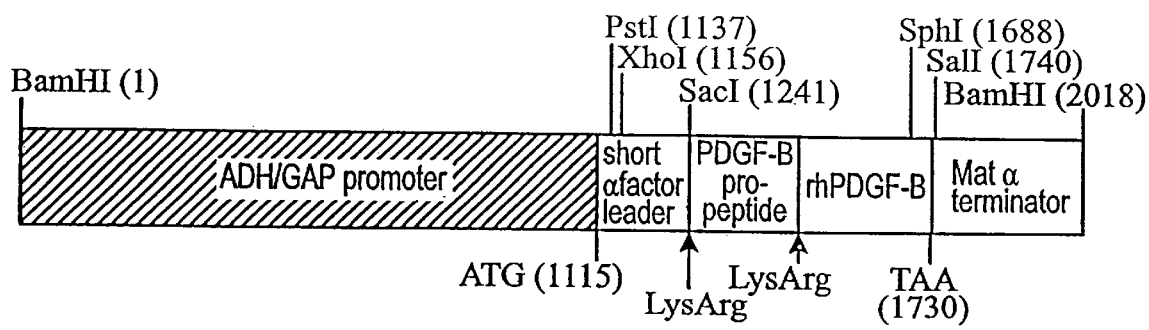
FIG. 4 is a map of the rhPDGF-B expression cassette in pL7PPB and pYL7PPB.

Plasmid pYL7PPB (also known as pYAGL7PPB) includes an expression cassette with the following features. Transcription initiation and termination is mediated by the inducible, hybrid yeast promoter ADH/GAP and the Matα transcriptional terminator described above. The gene further includes an open reading frame encoding a truncated yeast α-factor leader to mediate secretion of rhPDGF-BB. The propeptide sequence included in the expression construct is only the native N-terminal propeptide sequence; the native C-terminal propeptide sequence was not included in the construct. Inclusion of the N-terminal propeptide sequence resulted in enhanced expression of rhPDGF-BB, presumably because of improved folding. Dibasic processing sites at the truncated α-factor leader/N-terminal propeptide and N-terminal propeptide/PDGF-B junctions were included to facilitate production of correctly processed rhPDGF-BB polypeptide by yeast. FIG. 4 shows a map of the pYL7PPB expression cassette highlighting these features and the sites relevant to the construction of this expression cassette. The nucleotide sequence and predicted amino acid sequence of the open reading frame encoding the truncated α-factor leader-proPDGF-B primary translation product are shown in SEQ ID NO: 26 and SEQ ID NO: 27, respectively.

Sequential Construction of pYL7PPB

Source of rbPDGF-B cDNA

A cloned cDNA encoding native human preproPDGF-B, 8hPDGFb-17, was provided by collaborators Arne Östman and Carl Heldin. Isolation of the cDNA encoding hPDGF-B was achieved using a cDNA library prepared from RNA isolated from a human clonal glioma cell line, U-343 MGa Cl 2 (Östman et al. (1988) J. Biol. Chem. 263:16202–16208).

Construction of pSV7d-PDGF A103-B1

Plasmid pSV7d-PDGF A103-B1 was the source of the N-terminal propeptide-PDGF-B cDNA. The plasmid was constructed as described below.

The 3 kb Eco R1 PDGF-B cDNA insert from clone 8hPDGFb-17 was excised and cloned into the unique Eco RI site of the mammalian expression vector pSV7d to give plasmid phPDGFβ-1 (also known as pSV7d-PDGF-B1).

A mammalian plasmid, pSV7d-PDGF A103-β1, for the coexpression of both PDGF-A and -B chains from their respective cDNAs, was constructed as follows. Plasmid phPDGFβ-1 was digested with PstI under conditions favoring cleavage at one of the two plasmid PstI sites (desired single cleavage at site in ampicillin resistance gene of the pSV7d vector backbone) and ligated with PstI-digested pSV7d-PDGF-A103(D1). This latter plasmid is strictly analogous to the PDGF-B mammalian expression plasmid phPDGFβ-1, except that it includes cDNA encoding the long, 211 amino acid form of the PDGF-A chain rather than the PDGF-B chain cDNA. This plasmid contains a single PstI site in the ampicillin resistance gene of the pSV7d vector backbone.

Following transformation, bacterial colonies were screened for the presence of both PDGF-B and PDGF-A cDNA sequences with the respective or appropriately labeled EcoRI cDNA probes. Colonies positive for both PDGF-B and -A chain sequences were further screened by EcoRI digestion of plasmid DNA, and plasmid pSV7d-PDGF A103-B1, having a predicted EcoRI pattern, was identified.

Mutagenesis of hPDGF-B cDNA

The PDGF-B cDNA was mutagenized: (1) to introduce a SacI site enabling introduction of the truncated α-factor secretion leader, and (2) to change the hPDGF-B cDNA sequence encoding dibasic amino acids Arg-Arg to encode Lys-Arg. This dibasic combination is more efficiently cleaved than Arg-Arg by the yeast dibasic processing enzyme KEX2 endopeptidase. The template for mutagenesis was prepared as follows.

The ~3 kb EcoRI hPDGF-B cDNA was isolated from pSV7d-PDGF A103-B1 and inserted into the EcoRI site of pBR322 to give plasmid pPPB/6. The nucleotide sequence of the 2.7 kb PstI-EcoRI cDNA fragment was verified. The 0.9 kb PstI-NcoI cDNA fragment was inserted into the PstI-NcoI sites of M13 and the nucleotide sequence of the insert verified. A partial nucleotide sequence and the predicted amino acid sequence of the PDGF-B cDNA are given in SEQ ID NO: 28 and SEQ ID NO: 29, respectively.

A double mutagenesis of M13 PstI-NcoI PDGF-B cDNA fragment was performed by standard methods using the following primers. Primer 1 (SEQ ID NO: 30) introduces a SacI site; primer 2 (SEQ ID NO: 31) converts Arg-Arg to Lys-Arg at the propeptide/PDGF-B junction. Additional mutations are introduced to facilitate detection of mutagenized sequences by hybridization with the labeled primer. No changes resulted in the primary amino acid sequence by primer 1 mutagenesis; only the Arg⇒Lys amino acid change resulted from primer 2 mutagenesis. Mutant hPDGF-B inserts were detected by hybridization with both primer 1 and 2 radiolabeled probes. DNA sequence was verified, and RF (double-stranded) plasmid was prepared.

Construction of pL7PPB (pAGL7PPB)

Essentially, the steps described below result in the substitution of the XhoI-SalI portion of the PDGF-B expression cassette in pAGL7PB encoding the C-terminal portion of the truncated α-factor leader, the Lys-Arg dibasic processing site and PDGF-B (FIG. 2) with an XhoI-SalI gene fragment encoding the C-terminal portion of the truncated α-factor leader, a Lys-Arg dibasic processing site, the PDGF-B N-terminal propeptide, a Lys-Arg dibasic processing site, and PDGF-B. The sequences encoding the N-terminal PDGF-B propeptide and PDGF-B were derived from cDNA as described above. A map of the resulting expression cassette is shown in FIG. 4.

A 447 bp SacI-SphI fragment including most of the proPDGF-B gene was isolated from the M13 RF containing the modified preproPDGF-B cDNA. Synthetic oligonucleotides, including sequences encoding the C-terminal part of truncated α-factor leader, a Lys-Arg dibasic processing site, and the N-terminal portion of the PDGF-B propeptide (SEQ ID NOs: 32–33), were joined to give a fragment with a 3' SacI overhang. Synthetic oligonucleotides, Sph-Sal I/Sph-Sal II, including sequences encoding the last 14 amino acids of PDGF-B and stop codons were joined to give a SphI-SalI fragment (SEQ ID NOs: 34–35). These two sets of annealed oligonucleotides were ligated to the 447 bp SacI-SphI proPDGF gene fragment. This resulted in a gene fragment including sequences encoding the C-terminal part of truncated α-factor leader, a Lys-Arg dibasic processing site and proPDGF-B.

Synthetic oligonucleotides, including sequences encoding the middle amino acids of the treated α-factor leader were joined resulting in a fragment with a 5' XhoI overhang (SEQ ID NOs: 32–33). This annealed oligonucleotide was ligated with pAGL7PB that had been cut with XhoI (unique site in pAGL7PB plasmid that is in the expression cassette, see FIG. 2). Following oligonucleotide annealing, the modified plasmid was digested with SalI resulting in loss of the PAGL7PB XhoI-SalI fragment and resulting in a vector/gene fragment.

Figure 5:
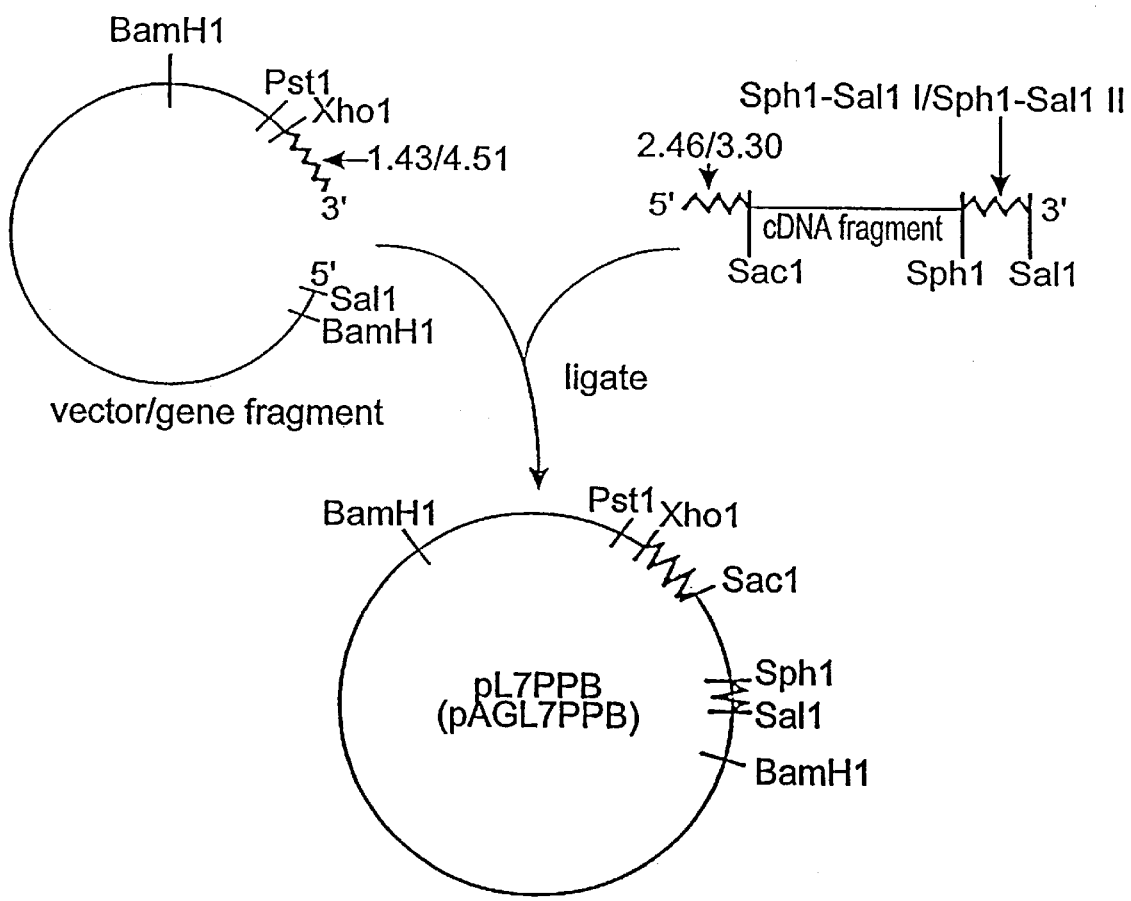
FIG. 5 shows the final steps in the construction of the rhPDGF-B expression cassette in pL7PPB.

The final step in the construction of the PDGF-B expression cassette was the ligation of the gene fragment into the vector/gene fragment to give plasmid pL7PPB (pAGL7PPB), as shown in FIG. 5. The PstI-BamH1 insert fragment was isolated and nucleotide sequencing confirmed that the desired construction had been obtained. A map of the PDGF-B expression cassette in pL7PPB is shown in FIG. 4.

Construction of pYL7PPB (pYAGL7PPB)

Figure 6:
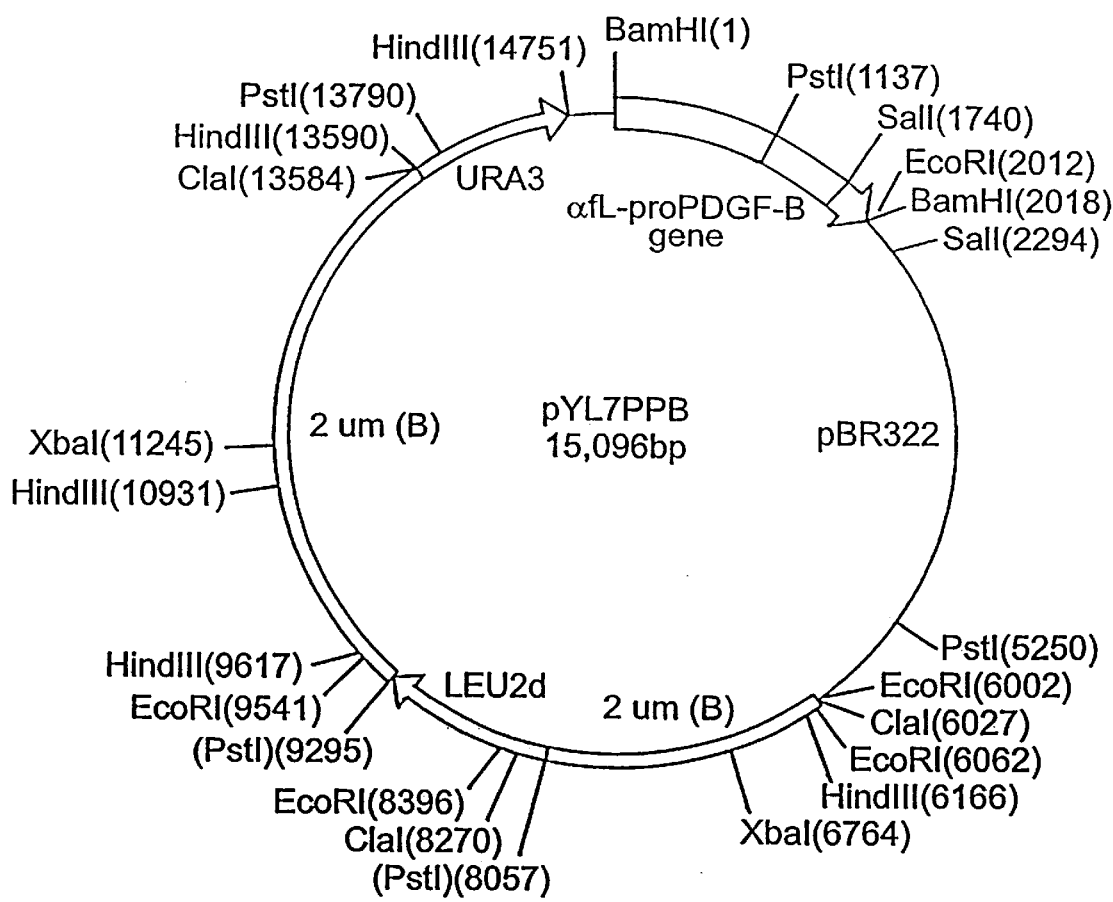
FIG. 6 is a map of rhPDGF-B expression plasmid pYL7PPB.

The PDGF-B expression cassette of pL7PPB was isolated following BamHI digestion and inserted into the BamHI site of the yeast shuttle vector pAB24, described above, resulting in yeast expression plasmid pYL7PPB. A map of pYL7PPB is shown in FIG. 6. The nucleotide sequence of the complete expression cassette and the predicted amino acid sequence of the open reading frame (ORF) encoding truncated α-factor leader-Lys-Arg-proPDGF-B are given in SEQ ID NO: 36 and SEQ ID NO: 37, respectively. The complete nucleotide sequence of yeast expression plasmid pYL7PPB has been determined.

Expression Strain Identification: MB2-1(pYL7PPB)

Expression plasmid pYL7PPB was transformed into S. cerevisiae MB2-1 by standard procedures and plasmid-harboring, uracil prototrophs were selected as isolated colonies. Individual colonies from independent transformants were screened for expression following inoculation of isolated colonies into growth medium that selects for leucine prototrophs. The medium also is high in glucose to keep expression of sequences under ADR2 regulation (including the PDGF-B gene) repressed. Cultures were subsequently diluted and grown to confluence in low glucose, selective growth medium lacking uracil. Cell-free supernatants were assayed for PDGF-BB by immunoactivity (ELISA) and by mitogenic activity on 3T3 cells. Frozen stocks were prepared of several transformants exhibiting consistently high levels of express ion. Following repeated testing, the transformant exhibiting, on aver age, the highest expression of PDGF-BB, MB2-1 (pYL7PPB #22) was selected.

Example 4

Expression Plasmid pYJST400

The Lys-Arg dibasic processing site between the α-factor leader sequence and the N-terminal propeptide was eliminated from expression plasmid pYL7PPB by in vitro mutagenesis to construct expression plasmid pYJST400. Thus pYJST400 has a single dibasic processing site, which resides at the propeptide/PDGF-B junction. Elimination of this first processing site was done to determine its relative effect on secretion of rhPDGF-BB from yeast as mediated by the α-factor leader peptide.

Example 5

Expression of Recombinant Human PDGF-BB

Recombinant human PDGF-BB is produced by a strain of the yeast, *Saccharomyces cerevisiae*, genetically modified with a multicopy yeast express ion plasmid that includes a gene encoding human PDGF-B. The preferred *S. cerevisiae* strain MB2-1 has the genotype: Matα ura3Δ, leu2–3, leu2–112, his3–11, his3–15, pep4Δ, [cir°]. It is auxotrophic for uracil, leucine, and histidine, requiring these nutritional supplements when grown in minimal medium. MB2-1 does not contain an endogenous 2-μ plasmid, which tends to interfere with the stability of the introduced plasimds and encourages recombination between endogenous and introduced plasmids. The strain does not express functional protease A, the product of the PEP4 gene, which interferes with the production of heterologous proteins. MB2-1 was designed to impart these favorable characteristics, which include selection for high expression of heterologous proteins.

Yeast expression plasmids pYAGL7PB, pYL7PPB, and pYJST400 were transformed into yeast strain MB2-1 as described by Hinnen et al. (1978) *Proc. Natl. Acad. Sci. USA* 75:1929–1933 and plated on ura-, 8% glucose, sorbitol plates. Transformants were grown in leu-, 8% glucose liquid medium for 24 hours and then plated onto leu-, 8% glucose sorbitol plates to get individual colonies. Individual colonies were picked and grown in 3 ml of leu-, 8% glucose medium for 24 hours at 30 C., and then inoculated (1:50) into 1 liter of ura-, 1% glucose media and grown for 75 hours at 30 C. Yeast culture medium was assayed for PDGF activity by the human foreskin fibroblast mitogen assay (see Example 5 below).

As shown in Table 1, inclusion of the sequence encoding the N-terminal propeptide resulted in a mean 3.4-fold increase in secretion of rhPDGF-BB as measured by bioactivity and by ELISA. Additionally, elimination of the Lys-Arg processing site at the leader/propeptide junction resulted in a 2.8-fold decrease in rhPDGF-BB secretion (Table 1).

These results indicate that the presence of the native N-terminal propeptide enhances secretion of biologically active mature rhPDGF-BB when flanked by preferred processing sites that have been modified for improved recognition by a proteolytic enzyme of the yeast host cell. Thus, cleavage at the leader/propeptide junction, as well as at the propeptide/PDGF-B junction, apparently facilitates the proper folding and/or processing and/or transport of the pro-PDGF-B, resulting in enhanced secretion of mature rhPDGF-BB.

Example 6

Human Foreskin Fibroblast (HFF) Mitogen Assay for PDGF

Human foreskin fibroblast stocks were stored frozen; freezing was at passage 13. Prior to use, HFF were thawed and then grown in T75 flasks until confluent, which usually occurred at 5–7 days. Growth medium contained Dulbecco's Modified Eagles Medium (DMEM), 20% fetal bovine serum (FBS), 1 mM sodium pyruvate, 300 μg/ml L-glutamine, 100 U/ml penicillin, and 100 μg/ml streptomycin. Cells were incubated at 37 C. in humidified 7% $CO_2$, 93% air atmosphere. At confluency, cells were passaged by rinsing the monolayer with phosphate buffered saline (PBS) lacking $C^{2+}$ and $Mg^{2+}$, dissociating them in trypsin containing EDTA, and diluting them with growth medium. Cells were passaged no more than 8 times after thawing.

To assay for PDGF, HFFs were plated as follows. The cells were rinsed and dissociated with trypsin as above. The trypsinized cells were pelleted and resuspended to a concentration of $1 \times 10^5$ cells/ml in medium similar to growth medium, except that 5% FBS replaced 20% FBS; 100 μl of suspension was dispensed into each well of a 96-well microtiter plate; and then the cells were incubated 5–6 days under the above described conditions.

PDGF in the sample was determined by monitoring $^3$H-thymidine incorporation into HFF DNA stimulated by PDGF. Samples were added to the wells containing HFF monolayers, and the assay plates incubated as above for 18 hours. The HFF cultures were then pulsed with [Methyl-$^3$H]thymidine (10 μC./ml final concentration, 1 μC./well) at 37 C. under the above described incubation conditions for 8 hours. After incubation, the cells were rinsed with PBS and fixed. Fixing was by incubation with 5% trichloracetic acid (TCA) and then 100% methanol for 15 minutes, followed by drying in air. The cells were then solubilized with 0.3N NaOH and then counted in a liquid scintillation counter.

Control samples were treated as the samples described above and were prepared as follows. For positive controls, PDGF, purchased from PDGF, Inc., was dissolved to a final concentration of 100 ng/ml in DMEM containing 10 mg/ml BSA. A standard curve was prepared; the first point was 10 ng/ml, the remaining points were 2-fold serial dilutions. Each dilution was tested in triplicate. Negative controls, which lacked both sample and control PDGF, were also run.

Example 7

Expression Plasmids pYLUI

Plasmid pYLUIGF24 includes an expression cassette with the hybrid yeast promoter ADH/GAP and Matα factor leader sequences fused to a sequence encoding the human IGF-I-A gene. This sequence was synthetically derived using yeast preferred codons. A dibasic amino acid processing site is present at the α-factor leader/IGF-I-A junction. The nucleotide sequence and predicted amino acid sequence of the open reading frame encoding α-factor leader/IGF-I-A primary translation product are given in SEQ ID NO: 38 and SEQ ID NO: 39, respectively.

Plasmid pYLUIGF34 differs from pYLUIGF24 only in its open reading frame. This cassette includes an open reading frame encoding a full length Matα factor leader sequence fused to a sequence encoding the human IGF-I-A gene with its C-terminal prosequence. Dibasic amino acid processing sites are present at the α-factor leader/IGF-I-A and IGF-I-A/IGF-I-A prosequence junctions. The nucleotide sequence and predicted amino acid sequence of the open reading frame encoding α-factor leader-proIGF-I-A primary translation product are given in SEQ ID NO: 40 and SEQ ID NO: 41, respectively.

Both of these plasmids were generated by inserting the respective expression cassette into the unique BamHI cloning site of the yeast shuttle vector pAB24 as described above.

Example 8

Expression of Recombinant Human IGF-I-A

Recombinant human IGF-I-A is produced by a strain of the yeast *Saccharomyces cerevisiae*, genetically modified with a multicopy yeast expression plasmid that includes a gene encoding human IGF-I-A. Yeast expression plasmids pYLUIGF24 and pYLUIGF34 were transformed into a yeast strain by procedures previously mentioned.

Western blot data indicated that properly processed IGF-I-A protein was obtained with the prosequence, modified KEX2 processing site, and a yeast secretion leader.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A vector comprising a nucleotide sequence that comprises in the 5' to 3' direction and operably linked (a) a yeast-recognized transcription and translation initiation region, (b) a coding sequence for a hybrid precursor polypeptide, and (c) a yeast-recognized transcription and translation termination region, wherein said hybrid precursor polypeptide comprises:

$$5'\text{-SP-(PS)}_{n-1}\text{-(LP-PS)}_{n-2}\text{-(NPRO}_{MHP}\text{-PS)}_{n-3}\text{-MHP-(PS-CPRO}_{M\text{-}HP})_{n-4}\text{-3}'$$

wherein:

SP comprises a signal peptide sequence for a yeast secreted protein;

PS comprises a preferred processing site cleaved in vivo by a yeast proteolytic enzyme;

LP comprises a leader peptide sequence for a yeast secreted protein;

NPRO$_{MHP}$ comprises a native N-terminal propeptide sequence of a mature heterologous mammalian protein of interest;

MHP comprises a peptide sequence for said mature heterologous mammalian protein of interest;

CPRO$_{MHP}$ comprises a native C-terminal propeptide sequence of said mature heterologous mammalian protein of interest; and n–1, n–2, n–3, and n–4 independently=0 or 1;

wherein said mammalian protein is a native PDGF-BB protein or variant thereof, wherein said variant has an amino acid sequence that has at least 70% sequence identity to the amino acid sequence of said native PDGF-BB protein, wherein said processing sites allow for proteolytic processing of said precursor polypeptide to said mature protein in vivo by a yeast host cell from the genus Kluyveromyces, and wherein at least n–3 or n–4=1.

2. The vector of claim 1, wherein n–2=1, n–3=1, and n–4=0.

3. The vector of claim 1, wherein LP is a truncated leader peptide sequence.

4. The vector of claim 1, wherein said yeast host cell is *Kluyveromyces lactis*.

5. A yeast host cell stably transformed with the vector of claim 1, wherein said yeast cell is from the genus Kluyveromyces.

6. A yeast host cell stably transformed with the vector of claim 2, wherein said yeast cell is from the genus Kluyveromyces.

7. A yeast host cell stably transformed with the vector of claim 3, wherein said yeast cell is from the genus Kluyveromyces.

8. A yeast host cell stably transformed with a vector, said vector comprising a nucleotide sequence that comprises in the 5' to 3' direction and operably linked (a) a yeast-recognized transcription and translation initiation region, (b) a coding sequence for a hybrid precursor polypeptide, and (c) a yeast-recognized transcription and translation termination region, wherein said hybrid precursor polypeptide has an amino acid sequence selected from the group consisting of the amino acid sequence set forth in SEQ ID NO:27 and an amino acid sequence having at least 70% sequence identity to the amino acid sequence set forth in SEQ ID NO: 27, wherein said yeast cell is from the genus Kluyveromyces.

9. The yeast host cell of claim 8, wherein said yeast host cell is *Kluyveromyces lactis*.

10. A method for expression of a heterologous protein and its secretion in the biologically active mature form using a yeast host cell from the genus Kluyveromyces as the expression system, said method comprising transforming said yeast cell with a vector comprising a nucleotide sequence that comprises in the 5' to 3' direction and operably linked (a) a yeast-recognized transcription and translation initiation region, (b) a coding sequence for a hybrid precursor polypeptide, and (c) a yeast-recognized transcription and translation termination region, wherein said hybrid precursor polypeptide comprises:

5'-SP-(PS)$_{n-1}$-(LP-PS)$_{n-2}$-(NPRO$_{MHP}$-PS)$_{n-3}$-MHP-(PS-CPRO$_{MHP}$)$_{n-4}$-3' wherein:

SP comprises a signal peptide sequence for a yeast secreted protein;

PS comprises a preferred processing site cleaved in vivo by a yeast proteolytic enzyme;

LP comprises a leader peptide sequence for a yeast secreted protein;

NPRO$_{MHP}$ comprises a native N-terminal propeptide sequence of a mature heterologous mammalian protein of interest;

MHP comprises a peptide sequence for said mature heterologous mammalian protein of interest;

CPRO$_{MHP}$ comprises a native C-terminal propeptide sequence of said mature heterologous mammalian protein of interest; and n–1, n–2, n–3, and n–4 independently=0 or 1;

wherein said mammalian protein is a native PDGF-BB protein or variant thereof, wherein said variant has an amino acid sequence that has at least 70% sequence identity to the amino acid sequence of said native PDGF-BB protein, wherein said processing sites allow for proteolytic processing of said precursor polypeptide to said mature protein in vivo by said yeast host cell, and wherein at least n–3 or n–4=1; and culturing said transformed cell such that said protein is expressed.

11. The method of claim 10, wherein said processing sites are dipeptides.

12. The method of claim 11, wherein said dipeptides are 5'-Lys-Arg-3'.

13. The method of claim 10, wherein said yeast host cell is *Kluyveromyces lactis*.

14. A method for expression of a heterologous protein and its secretion in the biologically active mature form using a yeast host cell from the genus Kluyveromyces as the expression system, said method comprising transforming said yeast cell with a vector comprising a nucleotide sequence that comprises in the 5' to 3' direction and operably linked (a) a yeast-recognized transcription and translation initiation region, (b) a coding sequence for a hybrid precursor polypeptide, and (c) a yeast-recognized transcription and translation termination region, wherein said hybrid precursor polypeptide comprises an amino acid sequence selected from the group consisting of the amino acid sequence set forth in SEQ ID NO: 27 and an amino acid sequence having at least about 70% sequence identity to the amino acid sequence set forth in SEQ ID NO: 27; and culturing said transformed cell such that said protein is expressed.

15. The method of claim 14, wherein said yeast host cell is *Kluyveromyces lactis*.

* * * * *

SEQUENCE LISTING (1) GENERAL INFORMATION:

(iii) NUMBER OF SEQUENCES: 41

(2) INFORMATION FOR SEQ ID NO: 1:

(i) SEQUENCE CHARACTERISTICS:
      (A) LENGTH: 444 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Chimeric nucleic acid"

(vi) ORIGINAL SOURCE:
      (A) ORGANISM: Homo sapiens/Saccharomyces cerevisiae (ix) FEATURE:
      (A) NAME/KEY: CDS
      (B) LOCATION: 1..441

(ix) FEATURE:
      (A) NAME/KEY: misc_feature
      (B) LOCATION: 1..111
      (D) OTHER INFORMATION: /function= "mediates secretion of
         proteins"
         /product= "yeast alpha factor leader peptide"
         /standard_name= "alpha factor signal/leader
         sequence"

(ix) FEATURE:
      (A) NAME/KEY: mat_peptide
      (B) LOCATION: 112..441
      (D) OTHER INFORMATION: /product= "rhPDGF-B protein"
         /standard_name= "rhPDGF-B"

(xi) SEQUENCE DESCRIPTION: SEQ ID NO: 1:

```
ATG AGA TTT CCT TCA ATT TTT ACT GCA GTT TTA TTC GCA GCC TCG AGC        48
Met Arg Phe Pro Ser Ile Phe Thr Ala Val Leu Phe Ala Ala Ser Ser
-37     -35              -30              -25

GCA TTA GCT GCT CCA GTC AAC ACT ACA ACA GAA GAT GAA ACG GCA CAA        96
Ala Leu Ala Ala Pro Val Asn Thr Thr Thr Glu Asp Glu Thr Ala Gln
    -20              -15              -10

ATT CCG GCT AAA AGA TCT TTG GGT TCT TTG ACT ATC GCT GAA CCA GCT       144
Ile Pro Ala Lys Arg Ser Leu Gly Ser Leu Thr Ile Ala Glu Pro Ala
 -5              1                5                10

ATG ATC GCT GAA TGT AAG ACT AGA ACT GAA GTT TTC GAA ATC TCC AGA       192
Met Ile Ala Glu Cys Lys Thr Arg Thr Glu Val Phe Glu Ile Ser Arg
             15               20               25

AGA TTG ATC GAC AGA ACT AAC GCT AAC TTC TTG GTT TGG CCA CCA TGT       240
Arg Leu Ile Asp Arg Thr Asn Ala Asn Phe Leu Val Trp Pro Pro Cys
         30               35               40
```

-continued

```
GTT GAA GTT CAA AGA TGT TCT GGT TGT TGT AAC AAC AGA AAC GTT CAA        288
Val Glu Val Gln Arg Cys Ser Gly Cys Cys Asn Asn Arg Asn Val Gln
    45                  50                  55

TGT AGA CCA ACT CAA GTT CAA TTG AGA CCA GTT CAA GTT AGA AAG ATC        336
Cys Arg Pro Thr Gln Val Gln Leu Arg Pro Val Gln Val Arg Lys Ile
60                  65                  70                  75

GAA ATC GTT AGA AAG AAG CCA ATC TTC AAG AAG GCT ACT GTT ACT TTG        384
Glu Ile Val Arg Lys Lys Pro Ile Phe Lys Lys Ala Thr Val Thr Leu
                80                  85                  90

GAA GAC CAC TTG GCT TGT AAG TGT GAA ACT GTC GCC GCT GCC AGG CCA        432
Glu Asp His Leu Ala Cys Lys Cys Glu Thr Val Ala Ala Ala Arg Pro
            95                  100                 105

GTT ACT TAA TAG                                                        444
Val Thr  *
        110
```

(2) INFORMATION FOR SEQ ID NO: 2:

(i) SEQUENCE CHARACTERISTICS:
        (A) LENGTH: 146 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Arg Phe Pro Ser Ile Phe Thr Ala Val Leu Phe Ala Ala Ser Ser
-37         -35                 -30                 -25

Ala Leu Ala Ala Pro Val Asn Thr Thr Thr Glu Asp Glu Thr Ala Gln
            -20                 -15                 -10

Ile Pro Ala Lys Arg Ser Leu Gly Ser Leu Thr Ile Ala Glu Pro Ala
-5                   1                   5                  10

Met Ile Ala Glu Cys Lys Thr Arg Thr Glu Val Phe Glu Ile Ser Arg
            15                  20                  25

Arg Leu Ile Asp Arg Thr Asn Ala Asn Phe Leu Val Trp Pro Pro Cys
            30                  35                  40

Val Glu Val Gln Arg Cys Ser Gly Cys Cys Asn Asn Arg Asn Val Gln
    45                  50                  55

Cys Arg Pro Thr Gln Val Gln Leu Arg Pro Val Gln Val Arg Lys Ile
60                  65                  70                  75

Glu Ile Val Arg Lys Lys Pro Ile Phe Lys Lys Ala Thr Val Thr Leu
                80                  85                  90

Glu Asp His Leu Ala Cys Lys Cys Glu Thr Val Ala Ala Ala Arg Pro
            95                  100                 105

Val Thr
```

(2) INFORMATION FOR SEQ ID NO: 3:

(i) SEQUENCE CHARACTERISTICS:
        (A) LENGTH: 352 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 3:

```
CTCTAGATAA AAGATCTTTG GGTTCTTTGA CTATCGCTGA ACCAGCTATG ATCGCTGAAT      60
```

```
GTAAGACTAG AACTGAAGTT TTCGAAATCT CCAGAAGATT GATCGACAGA ACTAACGCTA      120

ACTTCTTGGT TTGGCCACCA TGTGTTGAAG TTCAAAGATG TTCTGGTTGT TGTAACAACA      180

GAAACGTTCA ATGTAGACCA ACTCAAGTTC AATTGAGACC AGTTCAAGTT AGAAAGATCG      240

AAATCGTTAG AAAGAAGCCA ATCTTCAAGA AGGCTACTGT TACTTTGGAA GACCACTTGG      300

CTTGTAAGTG TGAAACTGTT GCTGGTGCTA GACCAGTTAC TTAATAGCGT CG             352
```

(2) INFORMATION FOR SEQ ID NO: 4:

(i) SEQUENCE CHARACTERISTICS:
        (A) LENGTH: 352 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Complementing strand to the (vi) ORIGINAL SOURCE:
        (A) ORGANISM: Homo sapiens (xi) SEQUENCE DESCRIPTION: SEQ ID NO: 4:

```
TCGACGACGC TATTAAGTAA CTGGTCTAGC AGCAGCAACA GTTTCACACT TACAAGCCAA       60

GTGGTCTTCC AAAGTAACAG TAGCCTTCTT GAAGATTGGC TTCTTTCTAA CGATTTCGAT      120

CTTTCTAACT TGAACTGGTC TCAATTGAAC TTGAGTTGGT CTACATTGAA CGTTTCTGTT      180

GTTACAACAA CCAGAACATC TTTGAACTTC AACACATGGT GGCCAAACCA AGAAGTTAGC      240

GTTAGTTCTG TCGATCGAAT CTTCTGGAGA TTTCGAAAAC TTAGTTCTAG TCTTACATTC      300

AGCGATCATA GCTGGTTCAG CGATAGTCAA AGAACCCAAA GATCTTTTAT CT             352
```

(2) INFORMATION FOR SEQ ID NO: 5:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 5:

```
CTCTAGATAA AAGATCTTTG GGTTCTTTGA CTATCGCTGA ACCA                        44
```

(2) INFORMATION FOR SEQ ID NO: 6:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 6:

```
GCTATGATCG CTGAATGTAA GACTAGAACT GAAGTTTTCG AAATC                       45
```

(2) INFORMATION FOR SEQ ID NO: 7:

```
    (i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 7:

TCCAGAAGAT TGATCGACAG AACTAACGCT AACTTCTTGG TTTGG                45

(2) INFORMATION FOR SEQ ID NO: 8:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 8:

CCACCATGTG TTGAAGTTCA AAGATGTTCT GGTTGTTGTA ACAAC                45

(2) INFORMATION FOR SEQ ID NO: 9:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 9:

AGAAACGTTC AATGTAGACC AACTCAAGTT CAATTGAGAC CAGTT                45

(2) INFORMATION FOR SEQ ID NO: 10:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 10:

CAAGTTAGAA AGATCGAAAT CGTTAGAAAG AAGCCAATCT TCAAG                45

(2) INFORMATION FOR SEQ ID NO: 11:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA
```

(vi) ORIGINAL SOURCE:
              (A) ORGANISM: Saccharomyces cerevisiae (xi) SEQUENCE DESCRIPTION: SEQ ID NO: 11:

AAGGCTACTG TTACTTTGGA AGACCACTTG GCTTGTAAGT GTGA                44

(2) INFORMATION FOR SEQ ID NO: 12:

(i) SEQUENCE CHARACTERISTICS:
              (A) LENGTH: 39 base pairs
              (B) TYPE: nucleic acid
              (C) STRANDEDNESS: single
              (D) TOPOLOGY: linear (ii) MOLECULE TYPE: cDNA (vi) ORIGINAL SOURCE:
              (A) ORGANISM: Homo sapiens (xi) SEQUENCE DESCRIPTION: SEQ ID NO: 12:

AACTGTTGCT GGTGCTAGAC CAGTTACTTA ATAGCGTCG                     39

(2) INFORMATION FOR SEQ ID NO: 13:

(i) SEQUENCE CHARACTERISTICS:
              (A) LENGTH: 18 base pairs
              (B) TYPE: nucleic acid
              (C) STRANDEDNESS: single
              (D) TOPOLOGY: linear (ii) MOLECULE TYPE: cDNA (vi) ORIGINAL SOURCE:
              (A) ORGANISM: Homo sapiens (xi) SEQUENCE DESCRIPTION: SEQ ID NO: 13:

TCTATTTTCT AGAAACCC                                            18

(2) INFORMATION FOR SEQ ID NO: 14:

(i) SEQUENCE CHARACTERISTICS:
              (A) LENGTH: 45 base pairs
              (B) TYPE: nucleic acid
              (C) STRANDEDNESS: single
              (D) TOPOLOGY: linear (ii) MOLECULE TYPE: cDNA (vi) ORIGINAL SOURCE:
              (A) ORGANISM: Homo sapiens (xi) SEQUENCE DESCRIPTION: SEQ ID NO: 14:

AAGAAACTGA TAGCGACTTG GTCGATACTA GCGACTTACA TTCTG              45

(2) INFORMATION FOR SEQ ID NO: 15:

(i) SEQUENCE CHARACTERISTICS:
              (A) LENGTH: 45 base pairs
              (B) TYPE: nucleic acid
              (C) STRANDEDNESS: single
              (D) TOPOLOGY: linear (ii) MOLECULE TYPE: cDNA (vi) ORIGINAL SOURCE:
              (A) ORGANISM: Homo sapiens (xi) SEQUENCE DESCRIPTION: SEQ ID NO: 15:

ATCTTGACTT CAAAAGCTTT AGAGGTCTTC TAACTAGCTG TCTTG              45

(2) INFORMATION FOR SEQ ID NO: 16:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 16:

```
ATTGCGATTG AAGAACCAAA CCGGTGGTAC ACAACTTCAA GTTTC           45
```

(2) INFORMATION FOR SEQ ID NO: 17:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 17:

```
TACAAGACCA CAAACATTGT TGTCTTTGCA AGTTACATCT GGTTG           45
```

(2) INFORMATION FOR SEQ ID NO: 18:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 18:

```
AGTTCAAGTT AACTCTGGTC AAGTTCAATC TTTCTAGCTT TAGCA           45
```

(2) INFORMATION FOR SEQ ID NO: 19:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO: 19:

```
ATCTTTCTTC GGTTAGAAGT TCTTCCGATG ACAATGAAAC CTTC            44
```

(2) INFORMATION FOR SEQ ID NO: 20:

(i) SEQUENCE CHARACTERISTICS:
        (A) LENGTH: 44 base pairs
        (B) TYPE: nucleic acid

```
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 20:

TGGTGAACCG AACATTCACA CTTTGACAAC GACGACGATC TGGT                44

(2) INFORMATION FOR SEQ ID NO: 21:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (xi) SEQUENCE DESCRIPTION: SEQ ID NO: 21:

CAATGAATTA TCGCAGCAGC T                                         21

(2) INFORMATION FOR SEQ ID NO: 22:

(i) SEQUENCE CHARACTERISTICS:
            (A) LENGTH: 81 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "Assembled synthetic (vi) ORIGINAL SOURCE:
            (A) ORGANISM: Synthetic (derived from Saccharomyces
                cerevisiae)

(xi) SEQUENCE DESCRIPTION: SEQ ID NO: 22:

TTTTATTCGC AGCCTCGAGC GCATTAGCTG CTCCAGTCAA CACTACAACA GAAGATGAAA    60

CGGCACAAAT TCCGGCTAAA A                                             81

(2) INFORMATION FOR SEQ ID NO: 23:

(i) SEQUENCE CHARACTERISTICS:
            (A) LENGTH: 90 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "This sequence is the (vi) ORIGINAL SOURCE:
            (A) ORGANISM: Synthetic (derived from Saccharomyces
                cerevisiae)

(xi) SEQUENCE DESCRIPTION: SEQ ID NO: 23:

GATCTTTTAG CCGGAATTTG TGCCGTTTCA TCTTCTGTTG TAGTGTTGAC TGGAGCAGCT    60

AATGCGCTCG AGGCTGCGAA TAAAACTGCA                                    90

(2) INFORMATION FOR SEQ ID NO: 24:

(i) SEQUENCE CHARACTERISTICS:
            (A) LENGTH: 1845 base pairs
```

-continued

```
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic chimera"

(vi) ORIGINAL SOURCE:
        (A) ORGANISM: Homo sapiens/Saccaromyces cerevisiae (ix) FEATURE:
        (A) NAME/KEY: CDS
        (B) LOCATION: 1115..1558

(ix) FEATURE:
        (A) NAME/KEY: promoter
        (B) LOCATION: 1..1114
        (D) OTHER INFORMATION: /standard_name= "ADH/GAP promoter"

(ix) FEATURE:
        (A) NAME/KEY: misc_feature
        (B) LOCATION: 1115..1225
        (D) OTHER INFORMATION: /function= "mediates secretion of
            rhPDGF-B"
            /product= "truncated alpha factor leader/signal
            peptide"
            /standard_name= "alpha factor leader/signal
            sequence"

(ix) FEATURE:
        (A) NAME/KEY: mat_peptide
        (B) LOCATION: 1226..1558
        (D) OTHER INFORMATION: /product= "rhPDGF-B peptide"
            /standard_name= "rhPDGF-B"

(xi) SEQUENCE DESCRIPTION: SEQ ID NO: 24:
```

| | |
|---|---|
| GGATCCTTCA ATATGCGCAC ATACGCTGTT ATGTTCAAGG TCCCTTCGTT TAAGAACGAA | 60 |
| AGCGGTCTTC CTTTTGAGGG ATGTTTCAAG TTGTTCAAAT CTATCAAATT TGCAAATCCC | 120 |
| CAGTCTGTAT CTAGCTAGAT ATACCAATGG CAAACTGAGC ACAACAATAC CAGTCCGGAT | 180 |
| CAACTGGCAC CATCTCTCCC GTAGTCTCAT CTAATTTTTC TTCCGGATGA GGTTCCAGAT | 240 |
| ATACCGCAAC ACCTTTATTA TGGTTTCCCT GAGGGAATAA TAGAATGTCC CATTCGAAAT | 300 |
| CACCAATTCT AAACCTGGGC GAATTGTATT TCGGGTTTGT TAACTCGTTC CAGTCAGGAA | 360 |
| TGTTCCACGT GAAGCTATCT TCCAGCAAAG TCTCCACTTC TTCATCAAAT TGTGGGAGAA | 420 |
| TACTCCCAAT GCTCTTATCT ATGGGACTTC CGGGAAACAC AGTACCGATA CTTCCCAATT | 480 |
| CGTCTTCAGA GCTCATTGTT TGTTTGAAGA GACTAATCAA AGAATCGTTT CTCAAAAAA | 540 |
| ATTAATATCT TAACTGATAG TTTGATCAAA GGGGCAAAAC GTAGGGGCAA ACAAACGGAA | 600 |
| AAATCGTTTC TCAAATTTTC TGATGCCAAG AACTCTAACC AGTCTTATCT AAAAATTGCC | 660 |
| TTATGATCCG TCTCTCCGGT TACAGCCTGT GTAACTGATT AATCCTGCCT TTCTAATCAC | 720 |
| CATTCTAATG TTTTAATTAA GGGATTTTGT CTTCATTAAC GGCTTTCGCT CATAAAAATG | 780 |
| TTATGACGTT TTGCCCGCAG GCGGGAAACC ATCCACTTCA CGAGACTGAT CTCCTCTGCC | 840 |
| GGAACACCGG GCATCTCCAA CTTATAAGTT GGAGAAATAA GAGAATTTCA GATTGAGAGA | 900 |
| ATGAAAAAAA AAACCCTGA AAAAAAAGGT TGAAACCAGT TCCCTGAAAT TATTCCCCTA | 960 |
| CTTGACTAAT AAGTATATAA AGACGGTAGG TATTGATTGT AATTCTGTAA ATCTATTTCT | 1020 |
| TAAACTTCTT AAATTCTACT TTTATAGTTA GTCTTTTTTT TAGTTTTAAA ACACCAAGAA | 1080 |
| CTTAGTTTCG AATAAACACA CATAAACAAA CACC ATG AGA TTT CCT TCA ATT | 1132 |
|                            Met Arg Phe Pro Ser Ile | |
|                            -37  -35 | |
| TTT ACT GCA GTT TTA TTC GCA GCC TCG AGC GCA TTA GCT GCT CCA GTC | 1180 |
| Phe Thr Ala Val Leu Phe Ala Ala Ser Ser Ala Leu Ala Ala Pro Val | |

```
                -30              -25               -20
AAC ACT ACA ACA GAA GAT GAA ACG GCA CAA ATT CCG GCT AAA AGA TCT       1228
Asn Thr Thr Thr Glu Asp Glu Thr Ala Gln Ile Pro Ala Lys Arg Ser
-15              -10                               -5                1

TTG GGT TCT TTG ACT ATC GCT GAA CCA GCT ATG ATC GCT GAA TGT AAG       1276
Leu Gly Ser Leu Thr Ile Ala Glu Pro Ala Met Ile Ala Glu Cys Lys
             5                   10                      15

ACT AGA ACT GAA GTT TTC GAA ATC TCC AGA AGA TTG ATC GAC AGA ACT       1324
Thr Arg Thr Glu Val Phe Glu Ile Ser Arg Arg Leu Ile Asp Arg Thr
         20                  25                  30

AAC GCT AAC TTC TTG GTT TGG CCA CCA TGT GTT GAA GTT CAA AGA TGT       1372
Asn Ala Asn Phe Leu Val Trp Pro Pro Cys Val Glu Val Gln Arg Cys
     35                  40                  45

TCT GGT TGT TGT AAC AAC AGA AAC GTT CAA TGT AGA CCA ACT CAA GTT       1420
Ser Gly Cys Cys Asn Asn Arg Asn Val Gln Cys Arg Pro Thr Gln Val
 50              55                  60                          65

CAA TTG AGA CCA GTT CAA GTT AGA AAG ATC GAA ATC GTT AGA AAG AAG       1468
Gln Leu Arg Pro Val Gln Val Arg Lys Ile Glu Ile Val Arg Lys Lys
                 70                  75                  80

CCA ATC TTC AAG AAG GCT ACT GTT ACT TTG GAA GAC CAC TTG GCT TGT       1516
Pro Ile Phe Lys Lys Ala Thr Val Thr Leu Glu Asp His Leu Ala Cys
             85                  90                  95

AAG TGT GAA ACT GTC GCC GCT GCC AGG CCA GTT ACT TAA TAG               1558
Lys Cys Glu Thr Val Ala Ala Ala Arg Pro Val Thr *   *
100                 105                 110

CGTCGTCGAC TTTGTTCCCA CTGTACTTTT AGCTCGTACA AAATACAATA TACTTTTCAT     1618

TTCTCCGTAA CAACATGTT TTCCCATGTA ATATCCTTTT CTATTTTTCG TTCCGTTACC      1678

AACTTTACAC ATACTTTATA TAGCTATTCA CTTCTATACA CTAAAAAACT AAGACAATTT     1738

TAATTTTGCT GCCTGCCATA TTTCAATTTG TTATAAATTC CTATAATTTA TCCTATTAGT     1798

AGCTAAAAAA AGATGAATGT GAATCGAATC CTAAGAGAAT TCGGATC                   1845

(2) INFORMATION FOR SEQ ID NO: 25:

(i) SEQUENCE CHARACTERISTICS:
        (A) LENGTH: 146 amino acids
        (B) TYPE: amino acid
        (D) TOPOLOGY: linear (ii) MOLECULE TYPE: protein (xi) SEQUENCE DESCRIPTION: SEQ ID NO: 25:

Met Arg Phe Pro Ser Ile Phe Thr Ala Val Leu Phe Ala Ala Ser Ser
-37         -35                 -30                 -25

Ala Leu Ala Ala Pro Val Asn Thr Thr Glu Asp Glu Thr Ala Gln
        -20                 -15                 -10

Ile Pro Ala Lys Arg Ser Leu Gly Ser Leu Thr Ile Ala Glu Pro Ala
 -5              1                   5                   10

Met Ile Ala Glu Cys Lys Thr Arg Thr Glu Val Phe Glu Ile Ser Arg
             15                  20                  25

Arg Leu Ile Asp Arg Thr Asn Ala Asn Phe Leu Val Trp Pro Pro Cys
         30                  35                  40

Val Glu Val Gln Arg Cys Ser Gly Cys Cys Asn Asn Arg Asn Val Gln
     45                  50                  55

Cys Arg Pro Thr Gln Val Gln Leu Arg Pro Val Gln Val Arg Lys Ile
 60                  65                  70                  75

Glu Ile Val Arg Lys Lys Pro Ile Phe Lys Lys Ala Thr Val Thr Leu
             80                  85                  90
```

-continued

```
Glu Asp His Leu Ala Cys Lys Cys Glu Thr Val Ala Ala Ala Arg Pro
         95                 100                 105
Val Thr (2) INFORMATION FOR SEQ ID NO: 26:

(i) SEQUENCE CHARACTERISTICS:
        (A) LENGTH: 621 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "This construct is a (vi) ORIGINAL SOURCE:
        (A) ORGANISM: Saccharomyces cerevisiae/Homo sapiens (ix) FEATURE:
        (A) NAME/KEY: CDS
        (B) LOCATION: 1..621

(ix) FEATURE:
        (A) NAME/KEY: misc_feature
        (B) LOCATION: 25..105
        (D) OTHER INFORMATION: /function= "Mediates secretion of
            human rhPDGF-B"
            /product= "Saccharomyces cerevisiae alpha-factor
            leader/signal sequence"

(ix) FEATURE:
        (A) NAME/KEY: transit_peptide
        (B) LOCATION: 112..288
        (D) OTHER INFORMATION: /function= "Mediates protein
            transport"
            /product= "human PDGF propeptide"

(ix) FEATURE:
        (A) NAME/KEY: mat_peptide
        (B) LOCATION: 289..621
        (D) OTHER INFORMATION: /product= "human PDGF-B peptide"
            /standard_name= "rhPDGF-B"

(xi) SEQUENCE DESCRIPTION: SEQ ID NO: 26:

ATG AGA TTT CCT TCA ATT TTT ACT GCA GTT TTA TTC GCA GCC TCG AGC        48
Met Arg Phe Pro Ser Ile Phe Thr Ala Val Leu Phe Ala Ala Ser Ser
-96 -95             -90                 -85

GCA TTA GCT GCT CCA GTC AAC ACT ACA ACA GAA GAT GAA ACG GCA CAA        96
Ala Leu Ala Ala Pro Val Asn Thr Thr Thr Glu Asp Glu Thr Ala Gln
-80                 -75                 -70                 -65

ATT CCG GCT AAA AGA GAC CCC ATT CCC GAG GAG CTC TAC GAG ATG CTG       144
Ile Pro Ala Lys Arg Asp Pro Ile Pro Glu Glu Leu Tyr Glu Met Leu
                -60                 -55                 -50

AGT GAC CAC TCG ATC CGC TCC TTT GAT GAT CTC CAA CGC CTG CTG CAC       192
Ser Asp His Ser Ile Arg Ser Phe Asp Asp Leu Gln Arg Leu Leu His
            -45                 -40                 -35

GGA GAC CCC GGA GAG GAA GAT GGG GCC GAG TTG GAC CTG AAC ATG ACC       240
Gly Asp Pro Gly Glu Glu Asp Gly Ala Glu Leu Asp Leu Asn Met Thr
        -30                 -25                 -20

CGC TCC CAC TCT GGA GGC GAG CTG GAG AGC TTG GCT CGG GGG AAG AGG       288
Arg Ser His Ser Gly Gly Glu Leu Glu Ser Leu Ala Arg Gly Lys Arg
    -15                 -10                  -5

AGC CTG GGT TCC CTG ACC ATT GCT GAG CCG GCC ATG ATC GCC GAG TGC       336
Ser Leu Gly Ser Leu Thr Ile Ala Glu Pro Ala Met Ile Ala Glu Cys
  1                   5                  10                  15

AAG ACG CGC ACC GAG GTG TTC GAG ATC TCC CGG CGC CTC ATA GAC CGC       384
Lys Thr Arg Thr Glu Val Phe Glu Ile Ser Arg Arg Leu Ile Asp Arg
                 20                  25                  30
```

```
ACC AAC GCC AAC TTC CTG GTG TGG CCG CCC TGT GTG GAG GTG CAG CGC    432
Thr Asn Ala Asn Phe Leu Val Trp Pro Pro Cys Val Glu Val Gln Arg
         35                  40                  45

TGC TCC GGC TGC TGC AAC AAC CGC AAC GTG CAG TGC CGC CCC ACC CAG    480
Cys Ser Gly Cys Cys Asn Asn Arg Asn Val Gln Cys Arg Pro Thr Gln
 50                  55                  60

GTG CAG CTG CGA CCT GTC CAG GTG AGA AAG ATC GAG ATT GTG CGG AAG    528
Val Gln Leu Arg Pro Val Gln Val Arg Lys Ile Glu Ile Val Arg Lys
 65                  70                  75                  80

AAG CCA ATC TTT AAG AAG GCC ACG GTG ACG CTG GAA GAC CAC CTG GCA    576
Lys Pro Ile Phe Lys Lys Ala Thr Val Thr Leu Glu Asp His Leu Ala
                 85                  90                  95

TGC AAG TGT GAG ACA GTG GCA GCT GCA CGG CCT GTG ACC TAA TAG        621
Cys Lys Cys Glu Thr Val Ala Ala Ala Arg Pro Val Thr  *   *
                100                 105                 110
```

(2) INFORMATION FOR SEQ ID NO: 27:

(i) SEQUENCE CHARACTERISTICS:
      (A) LENGTH: 205 amino acids
      (B) TYPE: amino acid
      (D) TOPOLOGY: linear (ii) MOLECULE TYPE: protein (xi) SEQUENCE DESCRIPTION: SEQ ID NO: 27:

```
Met Arg Phe Pro Ser Ile Phe Thr Ala Val Leu Phe Ala Ala Ser Ser
-96 -95                 -90                 -85

Ala Leu Ala Ala Pro Val Asn Thr Thr Thr Glu Asp Glu Thr Ala Gln
-80                 -75                 -70                 -65

Ile Pro Ala Lys Arg Asp Pro Ile Pro Glu Glu Leu Tyr Glu Met Leu
                -60                 -55                 -50

Ser Asp His Ser Ile Arg Ser Phe Asp Asp Leu Gln Arg Leu Leu His
                -45                 -40                 -35

Gly Asp Pro Gly Glu Glu Asp Gly Ala Glu Leu Asp Leu Asn Met Thr
                -30                 -25                 -20

Arg Ser His Ser Gly Gly Glu Leu Glu Ser Leu Ala Arg Gly Lys Arg
                -15                 -10                 -5

Ser Leu Gly Ser Leu Thr Ile Ala Glu Pro Ala Met Ile Ala Glu Cys
 1               5                  10                  15

Lys Thr Arg Thr Glu Val Phe Glu Ile Ser Arg Arg Leu Ile Asp Arg
                 20                  25                  30

Thr Asn Ala Asn Phe Leu Val Trp Pro Pro Cys Val Glu Val Gln Arg
                 35                  40                  45

Cys Ser Gly Cys Cys Asn Asn Arg Asn Val Gln Cys Arg Pro Thr Gln
 50                  55                  60

Val Gln Leu Arg Pro Val Gln Val Arg Lys Ile Glu Ile Val Arg Lys
 65                  70                  75                  80

Lys Pro Ile Phe Lys Lys Ala Thr Val Thr Leu Glu Asp His Leu Ala
                 85                  90                  95

Cys Lys Cys Glu Thr Val Ala Ala Ala Arg Pro Val Thr
                100                 105
```

(2) INFORMATION FOR SEQ ID NO: 28:

(i) SEQUENCE CHARACTERISTICS:
      (A) LENGTH: 1320 base pairs
      (B) TYPE: nucleic acid
      (C) STRANDEDNESS: single (D) TOPOLOGY: linear (ii) MOLECULE TYPE: other nucleic acid
          (A) DESCRIPTION: /desc = "Synthetic chimera"

(vi) ORIGINAL SOURCE:
          (A) ORGANISM: Homo sapiens/Saccharomyces cerevisiae (ix) FEATURE:
          (A) NAME/KEY: CDS
          (B) LOCATION: 454..1179

(ix) FEATURE:
          (A) NAME/KEY: misc_feature
          (B) LOCATION: 454..519
          (D) OTHER INFORMATION: /product= "PDGF-B prepeptide"
              /standard_name= "PDGF-B presequence"

(ix) FEATURE:
          (A) NAME/KEY: transit_peptide
          (B) LOCATION: 455..696
          (D) OTHER INFORMATION: /function= "mediates protein
              transport"
              /product= "PDGF-B propeptide"
              /standard_name= "PDGF-B prosequence"

(ix) FEATURE:
          (A) NAME/KEY: mat_peptide
          (B) LOCATION: 697..1023
          (D) OTHER INFORMATION: /product= "rhPDGF-B peptide"
              /standard_name= "rhPDGF-B"

(ix) FEATURE:
          (A) NAME/KEY: transit_peptide
          (B) LOCATION: 1024..1179
          (D) OTHER INFORMATION: /function= "mediates protein
              transport"
              /product= "PDGF-B propeptide"
              /standard_name= "PDGF-B prosequence"

(xi) SEQUENCE DESCRIPTION: SEQ ID NO: 28:

```
GAATTCCCAG AAAATGTTGC AAAAAAGCTA AGCCGGCGGG CAGAGGAAAA CGCCTGTAGC        60

CGGCGAGTGA AGACGAACCA TCGACTGCCG TGTTCCTTTT CCTCTTGGAG GTTGGAGTCC       120

CCTGGGCGCC CCCACACGGC TAGACGCCTC GGCTGGTTCG CGACGCAGCC CCCCGGCCGT       180

GGATGCTGCA CTCGGGCTCG GGATCCGCCC AGGTAGCGGC CTCGGACCCA GGTCCTGCGC       240

CCAGGTCCTC CCCTGCCCCC CAGCGACGGA GCCGGGGCCG GGGGCGGCGG CGCCGGGGGC       300

ATGCGGGTGA GCCGCGGCTG CAGAGGCCTG AGCGCCTGAT CGCCGCGGAC CCGAGCCGAG       360

CCCACCCCCC TCCCCAGCCC CCCACCCTGG CCGCGGGGGC GGCGCGCTCG ATCTACGCGT       420

TCGGGGCCCC GCGGGGCCGG GCCCGGAGTC GGC ATG AAT CGC TGC TGG GCG CTC       474
                                    Met Asn Arg Cys Trp Ala Leu
                                    -81 -80                 -75

TTC CTG TCT CTC TGC TGC TAC CTG CGT CTG GTC AGC GCC GAG GGG GAC        522
Phe Leu Ser Leu Cys Cys Tyr Leu Arg Leu Val Ser Ala Glu Gly Asp
                -70             -65             -60

CCC ATT CCC GAG GAG CTT TAT GAG ATG CTG AGT GAC CAC TCG ATC CGC        570
Pro Ile Pro Glu Glu Leu Tyr Glu Met Leu Ser Asp His Ser Ile Arg
            -55             -50             -45

TCC TTT GAT GAT CTC CAA CGC CTG CTG CAC GGA GAC CCC GGA GAG GAA        618
Ser Phe Asp Asp Leu Gln Arg Leu Leu His Gly Asp Pro Gly Glu Glu
        -40             -35             -30

GAT GGG GCC GAG TTG GAC CTG AAC ATG ACC CGC TCC CAC TCT GGA GGC        666
Asp Gly Ala Glu Leu Asp Leu Asn Met Thr Arg Ser His Ser Gly Gly
    -25             -20             -15

GAG CTG GAG AGC TTG GCT CGT GGA AGA AGG AGC CTG GGT TCC CTG ACC        714
Glu Leu Glu Ser Leu Ala Arg Gly Arg Arg Ser Leu Gly Ser Leu Thr
-10              -5                  1               5
```

```
ATT GCT GAG CCG GCC ATG ATC GCC GAG TGC AAG ACG CGC ACC GAG GTG         762
Ile Ala Glu Pro Ala Met Ile Ala Glu Cys Lys Thr Arg Thr Glu Val
             10                  15                  20

TTC GAG ATC TCC CGG CGC CTC ATA GAC CGC ACC AAC GCC AAC TTC CTG         810
Phe Glu Ile Ser Arg Arg Leu Ile Asp Arg Thr Asn Ala Asn Phe Leu
        25                  30                  35

GTG TGG CCG CCC TGT GTG GAG GTG CAG CGC TGC TCC GGC TGC TGC AAC         858
Val Trp Pro Pro Cys Val Glu Val Gln Arg Cys Ser Gly Cys Cys Asn
    40                  45                  50

AAC CGC AAC GTG CAG TGC CGC CCC ACC CAG GTG CAG CTG CGA CCT GTC         906
Asn Arg Asn Val Gln Cys Arg Pro Thr Gln Val Gln Leu Arg Pro Val
55                  60                  65                  70

CAG GTG AGA AAG ATC GAG ATT GTG CGG AAG AAG CCA ATC TTT AAG AAG         954
Gln Val Arg Lys Ile Glu Ile Val Arg Lys Lys Pro Ile Phe Lys Lys
                75                  80                  85

GCC ACG GTG ACG CTG GAA GAC CAC CTG GCA TGC AAG TGT GAG ACA GTG         1002
Ala Thr Val Thr Leu Glu Asp His Leu Ala Cys Lys Cys Glu Thr Val
            90                  95                  100

GCA GCT GCA CGG CCT GTG ACC CGA AGC CCG GGG GGT TCC CAG GAG CAG         1050
Ala Ala Ala Arg Pro Val Thr Arg Ser Pro Gly Gly Ser Gln Glu Gln
        105                 110                 115

CGA GCC AAA ACG CCC CAA ACT CGG GTG ACC ATT CGG ACG GTG CGA GTC         1098
Arg Ala Lys Thr Pro Gln Thr Arg Val Thr Ile Arg Thr Val Arg Val
    120                 125                 130

CGC CGG CCC CCC AAG GGC AAG CAC CGG AAA TTC AAG CAC ACG CAT GAC         1146
Arg Arg Pro Pro Lys Gly Lys His Arg Lys Phe Lys His Thr His Asp
135                 140                 145                 150

AAG ACG GCA CTG AAG GAG ACC CTT GGA GCC TAG GGGCATCGGC AGGAGAGT         1199
Lys Thr Ala Leu Lys Glu Thr Leu Gly Ala  *
                155                 160

GTGGGCAGGG TTATTTAATA TGGTATTTGT GTATTGCCCC CATGGGGCCT TGGAGTAGAT       1259

AATATTGTTT CCCTCGTCCG TCTGTCTCGA TGCCTGATTC GGACGGCCAA TGGTGCCTCC       1319

C                                                                       1320

(2) INFORMATION FOR SEQ ID NO: 29:

(i) SEQUENCE CHARACTERISTICS:
        (A) LENGTH: 241 amino acids
        (B) TYPE: amino acid
        (D) TOPOLOGY: linear (ii) MOLECULE TYPE: protein (xi) SEQUENCE DESCRIPTION: SEQ ID NO: 29:

Met Asn Arg Cys Trp Ala Leu Phe Leu Ser Leu Cys Cys Tyr Leu Arg
-81 -80                 -75                 -70

Leu Val Ser Ala Glu Gly Asp Pro Ile Pro Glu Glu Leu Tyr Glu Met
-65                 -60                 -55                 -50

Leu Ser Asp His Ser Ile Arg Ser Phe Asp Asp Leu Gln Arg Leu Leu
            -45                 -40                 -35

His Gly Asp Pro Gly Glu Glu Asp Gly Ala Glu Leu Asp Leu Asn Met
        -30                 -25                 -20

Thr Arg Ser His Ser Gly Gly Glu Leu Glu Ser Leu Ala Arg Gly Arg
    -15                 -10                 -5

Arg Ser Leu Gly Ser Leu Thr Ile Ala Glu Pro Ala Met Ile Ala Glu
1                   5                   10                  15

Cys Lys Thr Arg Thr Glu Val Phe Glu Ile Ser Arg Arg Leu Ile Asp
            20                  25                  30
```

```
Arg Thr Asn Ala Asn Phe Leu Val Trp Pro Pro Cys Val Glu Val Gln
            35                  40                  45

Arg Cys Ser Gly Cys Cys Asn Asn Arg Asn Val Gln Cys Arg Pro Thr
        50                  55                  60

Gln Val Gln Leu Arg Pro Val Gln Val Arg Lys Ile Glu Ile Val Arg
    65                  70                  75

Lys Lys Pro Ile Phe Lys Lys Ala Thr Val Thr Leu Glu Asp His Leu
80                  85                  90                  95

Ala Cys Lys Cys Glu Thr Val Ala Ala Arg Pro Val Thr Arg Ser
                100                 105                 110

Pro Gly Gly Ser Gln Glu Gln Arg Ala Lys Thr Pro Gln Thr Arg Val
                115                 120                 125

Thr Ile Arg Thr Val Arg Val Arg Arg Pro Pro Lys Gly Lys His Arg
            130                 135                 140

Lys Phe Lys His Thr His Asp Lys Thr Ala Leu Lys Glu Thr Leu Gly
    145                 150                 155

Ala
160
```

(2) INFORMATION FOR SEQ ID NO: 30:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Synthetic oligonucleotide"

(vi) ORIGINAL SOURCE:
        (A) ORGANISM: Synthetic (derived from Homo sapiens
            sequence)

(xi) SEQUENCE DESCRIPTION: SEQ ID NO: 30:

CATTCCCGAG GAGCTCTACG AGATGCTGAG TGAC                              34

(2) INFORMATION FOR SEQ ID NO: 31:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Synthetic oligonucleotide"

(vi) ORIGINAL SOURCE:
        (A) ORGANISM: Synthetic (derived from Homo sapiens
            sequence)

(xi) SEQUENCE DESCRIPTION: SEQ ID NO: 31:

CTTGGCTCGG GGGAAGAGGA GCCTGGG                                     27

(2) INFORMATION FOR SEQ ID NO: 32:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide"

(vi) ORIGINAL SOURCE:
            (A) ORGANISM: Homo sapiens/Saccharomyces cerevisiae derived
                sequence (ix) FEATURE:
            (A) NAME/KEY: misc_feature
            (B) LOCATION: 44..89
            (D) OTHER INFORMATION: /function= "truncated alpha factor
                leader/lys-arg proc./N-term. propept"

(xi) SEQUENCE DESCRIPTION: SEQ ID NO: 32:

TCGAGCGCAT TAGCTGCTCC AGTCAACACT ACAACAGAAG ATGAAACGGC ACAAATTCCG       60

GCTAAAAGAG ACCCCATTCC CGAGGAGCT                                        89

(2) INFORMATION FOR SEQ ID NO: 33:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide"

(vi) ORIGINAL SOURCE:
        (A) ORGANISM: Homo sapiens derived sequence (ix) FEATURE:
        (A) NAME/KEY: misc_feature
        (B) LOCATION: 1..39
        (D) OTHER INFORMATION: /function= "C-term.alpha factor
            leader/lys-arg proc./N-term. propeptide"

(xi) SEQUENCE DESCRIPTION: SEQ ID NO: 33:

CCTCGGGAAT GGGGTCTCTT TTAGCCGGAA TTTGTGCCGT TCATCTTCT GTTGTAGTGT        60

TGACTGGAGC AGCTAATGCG C                                                81

(2) INFORMATION FOR SEQ ID NO: 34:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide"

(vi) ORIGINAL SOURCE:
        (A) ORGANISM: Homo sapiens derived sequence (xi) SEQUENCE DESCRIPTION: SEQ ID NO: 34:

CAAGTGTGAG ACAGTGGCAG CTGCACGGCC TGTGACCTAA TAGCGTCG                    48

(2) INFORMATION FOR SEQ ID NO: 35:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide"

(vi) ORIGINAL SOURCE:
        (A) ORGANISM: Homo sapiens derived sequence (xi) SEQUENCE DESCRIPTION: SEQ ID NO: 35:

```
TCGACGACGC TATTAGGTCA CAGGCCGTGC AGCTGCCACT GTCTCACACT TGCATG          56
```

(2) INFORMATION FOR SEQ ID NO: 36:

(i) SEQUENCE CHARACTERISTICS:
        (A) LENGTH: 2023 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic chimera"

(vi) ORIGINAL SOURCE:
        (A) ORGANISM: Homo sapiens/Saccharomyces cerevisiae (ix) FEATURE:
        (A) NAME/KEY: CDS
        (B) LOCATION: 1115..1735

(ix) FEATURE:
        (A) NAME/KEY: promoter
        (B) LOCATION: 1..1114
        (D) OTHER INFORMATION: /standard_name= "ADH/GAP promoter"

(ix) FEATURE:
        (A) NAME/KEY: misc_feature
        (B) LOCATION: 1115..1225
        (D) OTHER INFORMATION: /function= "mediates secretion of
            rhPDGF-B"
            /product= "alpha factor signal/truncated alpha
            factor leader peptide"
            /standard_name= "truncated alpha factor
            signal/leader sequence"

(ix) FEATURE:
        (A) NAME/KEY: transit_peptide
        (B) LOCATION: 1226..1402
        (D) OTHER INFORMATION: /product= "PDGF-B propeptide"
            /standard_name= "PDGF-B prosequence"

(ix) FEATURE:
        (A) NAME/KEY: mat_peptide
        (B) LOCATION: 1403..1735
        (D) OTHER INFORMATION: /product= "rhPDGF-B protein"
            /standard_name= "rhPDGF-B"

(xi) SEQUENCE DESCRIPTION: SEQ ID NO: 36:

```
GGATCCTTCA ATATGCGCAC ATACGCTGTT ATGTTCAAGG TCCCTTCGTT TAAGAACGAA          60

AGCGGTCTTC CTTTTGAGGG ATGTTTCAAG TTGTTCAAAT CTATCAAATT TGCAAATCCC         120

CAGTCTGTAT CTAGCTAGAT ATACCAATGG CAAACTGAGC ACAACAATAC CAGTCCGGAT         180

CAACTGGCAC CATCTCTCCC GTAGTCTCAT CTAATTTTTC TTCCGGATGA GGTTCCAGAT         240

ATACCGCAAC ACCTTTATTA TGGTTTCCCT GAGGGAATAA TAGAATGTCC CATTCGAAAT         300

CACCAATTCT AAACCTGGGC GAATTGTATT TCGGGTTTGT TAACTCGTTC CAGTCAGGAA         360

TGTTCCACGT GAAGCTATCT TCCAGCAAAG TCTCCACTTC TTCATCAAAT TGTGGGAGAA         420

TACTCCCAAT GCTCTTATCT ATGGGACTTC CGGGAAACAC AGTACCGATA CTTCCCAATT         480

CGTCTTCAGA GCTCATTGTT TGTTTGAAGA GACTAATCAA AGAATCGTTT CTCAAAAAA          540

ATTAATATCT TAACTGATAG TTTGATCAAA GGGGCAAAAC GTAGGGGCAA ACAAACGGAA         600

AAATCGTTTC TCAAATTTTC TGATGCCAAG AACTCTAACC AGTCTTATCT AAAAATTGCC         660

TTATGATCCG TCTCTCCGGT TACAGCCTGT GTAACTGATT AATCCTGCCT TCTAATCAC          720

CATTCTAATG TTTTAATTAA GGGATTTTGT CTTCATTAAC GGCTTTCGCT CATAAAAATG         780

TTATGACGTT TTGCCCGCAG GCGGGAAACC ATCCACTTCA CGAGACTGAT CTCCTCTGCC         840
```

```
                                                        -continued

GGAACACCGG GCATCTCCAA CTTATAAGTT GGAGAAATAA GAGAATTTCA GATTGAGAGA       900

ATGAAAAAAA AAAACCCTGA AAAAAAAGGT TGAAACCAGT TCCCTGAAAT TATTCCCCTA       960

CTTGACTAAT AAGTATATAA AGACGGTAGG TATTGATTGT AATTCTGTAA ATCTATTTCT      1020

TAAACTTCTT AAATTCTACT TTTATAGTTA GTCTTTTTTT TAGTTTTAAA ACACCAAGAA      1080

CTTAGTTTCG AATAAACACA CATAAACAAA CACC ATG AGA TTT CCT TCA ATT         1132
                                    Met Arg Phe Pro Ser Ile
                                    -96 -95

TTT ACT GCA GTT TTA TTC GCA GCC TCG AGC GCA TTA GCT GCT CCA GTC       1180
Phe Thr Ala Val Leu Phe Ala Ala Ser Ser Ala Leu Ala Ala Pro Val
-90             -85             -80             -75

AAC ACT ACA ACA GAA GAT GAA ACG GCA CAA ATT CCG GCT AAA AGA GAC       1228
Asn Thr Thr Thr Glu Asp Glu Thr Ala Gln Ile Pro Ala Lys Arg Asp
            -70             -65             -60

CCC ATT CCC GAG GAG CTC TAC GAG ATG CTG AGT GAC CAC TCG ATC CGC       1276
Pro Ile Pro Glu Glu Leu Tyr Glu Met Leu Ser Asp His Ser Ile Arg
        -55             -50             -45

TCC TTT GAT GAT CTC CAA CGC CTG CTG CAC GGA GAC CCC GGA GAG GAA       1324
Ser Phe Asp Asp Leu Gln Arg Leu Leu His Gly Asp Pro Gly Glu Glu
    -40             -35             -30

GAT GGG GCC GAG TTG GAC CTG AAC ATG ACC CGC TCC CAC TCT GGA GGC       1372
Asp Gly Ala Glu Leu Asp Leu Asn Met Thr Arg Ser His Ser Gly Gly
    -25             -20             -15

GAG CTG GAG AGC TTG GCT CGG GGG AAG AGG AGC CTG GGT TCC CTG ACC       1420
Glu Leu Glu Ser Leu Ala Arg Gly Lys Arg Ser Leu Gly Ser Leu Thr
-10             -5              1               5

ATT GCT GAG CCG GCC ATG ATC GCC GAG TGC AAG ACG CGC ACC GAG GTG       1468
Ile Ala Glu Pro Ala Met Ile Ala Glu Cys Lys Thr Arg Thr Glu Val
                10              15              20

TTC GAG ATC TCC CGG CGC CTC ATA GAC CGC ACC AAC GCC AAC TTC CTG       1516
Phe Glu Ile Ser Arg Arg Leu Ile Asp Arg Thr Asn Ala Asn Phe Leu
            25              30              35

GTG TGG CCG CCC TGT GTG GAG GTG CAG CGC TGC TCC GGC TGC TGC AAC       1564
Val Trp Pro Pro Cys Val Glu Val Gln Arg Cys Ser Gly Cys Cys Asn
        40              45              50

AAC CGC AAC GTG CAG TGC CGC CCC ACC CAG GTG CAG CTG CGA CCT GTC       1612
Asn Arg Asn Val Gln Cys Arg Pro Thr Gln Val Gln Leu Arg Pro Val
55              60              65              70

CAG GTG AGA AAG ATC GAG ATT GTG CGG AAG AAG CCA ATC TTT AAG AAG       1660
Gln Val Arg Lys Ile Glu Ile Val Arg Lys Lys Pro Ile Phe Lys Lys
                75              80              85

GCC ACG GTG ACG CTG GAA GAC CAC CTG GCA TGC AAG TGT GAG ACA GTG       1708
Ala Thr Val Thr Leu Glu Asp His Leu Ala Cys Lys Cys Glu Thr Val
            90              95              100

GCA GCT GCA CGG CCT GTG ACC TAA TAG CGTCGTCGAC TTTGTTCCCA             1755
Ala Ala Ala Arg Pro Val Thr *   *
            105             110

CTGTACTTTT AGCTCGTACA AAATACAATA TACTTTTCAT TTCTCCGTAA ACAACATGTT     1815

TTCCCATGTA ATATCCTTTT CTATTTTTCG TTCCGTTACC AACTTTACAC ATACTTTATA     1875

TAGCTATTCA CTTCTATACA CTAAAAAACT AAGACAATTT TAATTTTGCT GCCTGCCATA     1935

TTTCAATTTG TTATAAATTC CTATAATTTA TCCTATTAGT AGCTAAAAAA AGATGAATGT     1995

GAATCGAATC CTAAGAGAAT TCGGATCC                                        2023
```

(2) INFORMATION FOR SEQ ID NO: 37:

(i) SEQUENCE CHARACTERISTICS:
        (A) LENGTH: 205 amino acids (B) TYPE: amino acid
        (D) TOPOLOGY: linear (ii) MOLECULE TYPE: protein (xi) SEQUENCE DESCRIPTION: SEQ ID NO: 37:

Met Arg Phe Pro Ser Ile Phe Thr Ala Val Leu Phe Ala Ala Ser Ser
-96     -95             -90             -85

Ala Leu Ala Ala Pro Val Asn Thr Thr Thr Glu Asp Glu Thr Ala Gln
-80             -75             -70             -65

Ile Pro Ala Lys Arg Asp Pro Ile Pro Glu Glu Leu Tyr Glu Met Leu
            -60             -55             -50

Ser Asp His Ser Ile Arg Ser Phe Asp Asp Leu Gln Arg Leu Leu His
            -45             -40             -35

Gly Asp Pro Gly Glu Glu Asp Gly Ala Glu Leu Asp Leu Asn Met Thr
            -30             -25             -20

Arg Ser His Ser Gly Gly Glu Leu Glu Ser Leu Ala Arg Gly Lys Arg
    -15             -10             -5

Ser Leu Gly Ser Leu Thr Ile Ala Glu Pro Ala Met Ile Ala Glu Cys
1               5               10              15

Lys Thr Arg Thr Glu Val Phe Glu Ile Ser Arg Arg Leu Ile Asp Arg
                20              25              30

Thr Asn Ala Asn Phe Leu Val Trp Pro Pro Cys Val Glu Val Gln Arg
            35              40              45

Cys Ser Gly Cys Cys Asn Asn Arg Asn Val Gln Cys Arg Pro Thr Gln
        50              55              60

Val Gln Leu Arg Pro Val Gln Val Arg Lys Ile Glu Ile Val Arg Lys
65              70              75              80

Lys Pro Ile Phe Lys Lys Ala Thr Val Thr Leu Glu Asp His Leu Ala
            85              90              95

Cys Lys Cys Glu Thr Val Ala Ala Arg Pro Val Thr
            100             105

(2) INFORMATION FOR SEQ ID NO: 38:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Chimeric DNA molecule"

(vi) ORIGINAL SOURCE:
        (A) ORGANISM: Homo sapiens/Saccharomyces cerevisiae (ix) FEATURE:
        (A) NAME/KEY: CDS
        (B) LOCATION: 1..471

(ix) FEATURE:
        (A) NAME/KEY: misc_feature
        (B) LOCATION: 1..255
        (D) OTHER INFORMATION: /function= "mediates protein
            secretion"
            /product= "Yeast alpha factor leader peptide"
            /standard_name= "Alpha factor signal/leader
            sequence"

(ix) FEATURE:
        (A) NAME/KEY: mat_peptide
        (B) LOCATION: 256..471
        (D) OTHER INFORMATION: /product= "rhIGF-I-A protein"
            /standard_name= "rhIGF-I-A"

(xi) SEQUENCE DESCRIPTION: SEQ ID NO: 38:

```
ATG AGA TTT CCT TCA ATT TTT ACT GCA GTT TTA TTC GCA GCA TCC TCC         48
Met Arg Phe Pro Ser Ile Phe Thr Ala Val Leu Phe Ala Ala Ser Ser
-85             -80                 -75                 -70

GCA TTA GCT GCT CCA GTC AAC ACT ACA GAA GAT GAA ACG GCA CAA             96
Ala Leu Ala Ala Pro Val Asn Thr Thr Thr Glu Asp Glu Thr Ala Gln
                -65                 -60                 -55

ATT CCG GCT GAA GCT GTC ATC GGT TAC TTA GAT TTA GAA GGG GAT TTC        144
Ile Pro Ala Glu Ala Val Ile Gly Tyr Leu Asp Leu Glu Gly Asp Phe
            -50                 -45                 -40

GAT GTT GCT GTT TTG CCA TTT TCC AAC AGC ACA AAT AAC GGG TTA TTG        192
Asp Val Ala Val Leu Pro Phe Ser Asn Ser Thr Asn Asn Gly Leu Leu
        -35                 -30                 -25

TTT ATA AAT ACT ACT ATT GCC AGC ATT GCT GCT AAA GAA GAA GGG GTA        240
Phe Ile Asn Thr Thr Ile Ala Ser Ile Ala Ala Lys Glu Glu Gly Val
    -20                 -15                 -10

CAG CTG GAT AAA AGA GGT CCA GAA ACC TTG TGT GGT GCT GAA TTG GTC        288
Gln Leu Asp Lys Arg Gly Pro Glu Thr Leu Cys Gly Ala Glu Leu Val
-5                   1               5                  10

GAT GCT TTG CAA TTC GTT TGT GGT GAC AGA GGT TTC TAC TTC AAC AAG        336
Asp Ala Leu Gln Phe Val Cys Gly Asp Arg Gly Phe Tyr Phe Asn Lys
            15                  20                  25

CCA ACC GGT TAC GGT TCT TCT TCT AGA AGA GCT CCA CAA ACC GGT ATC        384
Pro Thr Gly Tyr Gly Ser Ser Ser Arg Arg Ala Pro Gln Thr Gly Ile
        30                  35                  40

GTT GAC GAA TGT TGT TTC AGA TCT TGT GAC TTG AGA AGA TTG GAA ATG        432
Val Asp Glu Cys Cys Phe Arg Ser Cys Asp Leu Arg Arg Leu Glu Met
    45                  50                  55

TAC TGT GCT CCA TTG AAG CCA GCT AAG TCT GCT TGA TAA GTCGACTTT          480
Tyr Cys Ala Pro Leu Lys Pro Ala Lys Ser Ala  *   *
60                  65                  70
```

(2) INFORMATION FOR SEQ ID NO: 39:

(i) SEQUENCE CHARACTERISTICS:
        (A) LENGTH: 155 amino acids
        (B) TYPE: amino acid
        (D) TOPOLOGY: linear (ii) MOLECULE TYPE: protein (xi) SEQUENCE DESCRIPTION: SEQ ID NO: 39:

```
Met Arg Phe Pro Ser Ile Phe Thr Ala Val Leu Phe Ala Ala Ser Ser
-85             -80                 -75                 -70

Ala Leu Ala Ala Pro Val Asn Thr Thr Thr Glu Asp Glu Thr Ala Gln
                -65                 -60                 -55

Ile Pro Ala Glu Ala Val Ile Gly Tyr Leu Asp Leu Glu Gly Asp Phe
            -50                 -45                 -40

Asp Val Ala Val Leu Pro Phe Ser Asn Ser Thr Asn Asn Gly Leu Leu
        -35                 -30                 -25

Phe Ile Asn Thr Thr Ile Ala Ser Ile Ala Ala Lys Glu Glu Gly Val
    -20                 -15                 -10

Gln Leu Asp Lys Arg Gly Pro Glu Thr Leu Cys Gly Ala Glu Leu Val
-5                   1               5                  10

Asp Ala Leu Gln Phe Val Cys Gly Asp Arg Gly Phe Tyr Phe Asn Lys
            15                  20                  25

Pro Thr Gly Tyr Gly Ser Ser Ser Arg Arg Ala Pro Gln Thr Gly Ile
        30                  35                  40
```

```
Val Asp Glu Cys Cys Phe Arg Ser Cys Asp Leu Arg Arg Leu Glu Met
    45                  50                  55
Tyr Cys Ala Pro Leu Lys Pro Ala Lys Ser Ala
60                  65                  70
```

(2) INFORMATION FOR SEQ ID NO: 40:

(i) SEQUENCE CHARACTERISTICS:
        (A) LENGTH: 621 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Chimeric DNA molecule"

(vi) ORIGINAL SOURCE:
        (A) ORGANISM: Homo sapiens/Saccharomyces cerevisiae (ix) FEATURE:
        (A) NAME/KEY: CDS
        (B) LOCATION: 1..579

(ix) FEATURE:
        (A) NAME/KEY: misc_feature
        (B) LOCATION: 1..255
        (D) OTHER INFORMATION: /function= "mediates secretion of
            protein"
            /product= "3'end of yeast alpha factor leader
            peptide"
            /standard_name= "alpha factor leader/signal
            sequence"

(ix) FEATURE:
        (A) NAME/KEY: mat_peptide
        (B) LOCATION: 256..471
        (D) OTHER INFORMATION: /product= "rhIGF-I-A protein"
            /standard_name= "rhIGF-I-A"

(ix) FEATURE:
        (A) NAME/KEY: transit_peptide
        (B) LOCATION: 472..579
        (D) OTHER INFORMATION: /function= "mediates protein
            transport/translocation"
            /product= "IGF-I-A propeptide"
            /standard_name= "IGF-I-A prosequence"

(xi) SEQUENCE DESCRIPTION: SEQ ID NO: 40:

```
ATG AGA TTT CCT TCA ATT TTT ACT GCA GTT TTA TTC GCA GCA TCC TCC        48
Met Arg Phe Pro Ser Ile Phe Thr Ala Val Leu Phe Ala Ala Ser Ser
-85              -80                 -75                 -70

GCA TTA GCT GCT CCA GTC AAC ACT ACA ACA GAA GAT GAA ACG GCA CAA        96
Ala Leu Ala Ala Pro Val Asn Thr Thr Thr Glu Asp Glu Thr Ala Gln
            -65                 -60                 -55

ATT CCG GCT GAA GCT GTC ATC GGT TAC TTA GAT TTA GAA GGG GAT TTC       144
Ile Pro Ala Glu Ala Val Ile Gly Tyr Leu Asp Leu Glu Gly Asp Phe
        -50                 -45                 -40

GAT GTT GCT GTT TTG CCA TTT TCC AAC AGC ACA AAT AAC GGG TTA TTG       192
Asp Val Ala Val Leu Pro Phe Ser Asn Ser Thr Asn Asn Gly Leu Leu
    -35                 -30                 -25

TTT ATA AAT ACT ACT ATT GCC AGC ATT GCT GCT AAA GAA GAA GGG GTA       240
Phe Ile Asn Thr Thr Ile Ala Ser Ile Ala Ala Lys Glu Glu Gly Val
        -20                 -15                 -10

CAG CTG GAT AAA AGA GGT CCA GAA ACC TTG TGT GGT GCT GAA TTG GTC       288
Gln Leu Asp Lys Arg Gly Pro Glu Thr Leu Cys Gly Ala Glu Leu Val
    -5                1                   5                   10

GAT GCT TTG CAA TTC GTT TGT GGT GAC AGA GGT TTC TAC TTC AAC AAG       336
Asp Ala Leu Gln Phe Val Cys Gly Asp Arg Gly Phe Tyr Phe Asn Lys
                15                  20                  25
```

-continued

```
CCA ACC GGT TAC GGT TCT TCT TCT AGA AGA GCT CCA CAA ACC GGT ATC      384
Pro Thr Gly Tyr Gly Ser Ser Ser Arg Arg Ala Pro Gln Thr Gly Ile
            30                  35                  40

GTT GAC GAA TGT TGT TTC AGA TCT TGT GAC TTG AGA AGA TTG GAA ATG      432
Val Asp Glu Cys Cys Phe Arg Ser Cys Asp Leu Arg Arg Leu Glu Met
        45                  50                  55

TAC TGT GCT CCA TTG AAG CCT GCT AAG TCT GCT AAA AGA TCC GTC AGA      480
Tyr Cys Ala Pro Leu Lys Pro Ala Lys Ser Ala Lys Arg Ser Val Arg
 60                  65                  70                  75

GCT CAA AGA CAC ACC GAT ATG CCA AAG ACC CAA AAG GAA GTT CAC TTG      528
Ala Gln Arg His Thr Asp Met Pro Lys Thr Gln Lys Glu Val His Leu
                80                  85                  90

AAG AAC GCT TCC AGA GGT TCT GCT GGT AAC AAG AAC TAC AGA ATG TGA      576
Lys Asn Ala Ser Arg Gly Ser Ala Gly Asn Lys Asn Tyr Arg Met  *
            95                 100                 105

TAA GTCGACTTTG TTCCCACTGT ACTTTTAGCT CGTACAAAAT AC                   621
 *
```

(2) INFORMATION FOR SEQ ID NO: 41:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO: 41:

```
Met Arg Phe Pro Ser Ile Phe Thr Ala Val Leu Phe Ala Ala Ser Ser
-85                 -80                 -75                 -70

Ala Leu Ala Ala Pro Val Asn Thr Thr Thr Glu Asp Glu Thr Ala Gln
            -65                 -60                 -55

Ile Pro Ala Glu Ala Val Ile Gly Tyr Leu Asp Leu Glu Gly Asp Phe
        -50                 -45                 -40

Asp Val Ala Val Leu Pro Phe Ser Asn Ser Thr Asn Asn Gly Leu Leu
            -35                 -30                 -25

Phe Ile Asn Thr Thr Ile Ala Ser Ile Ala Ala Lys Glu Glu Gly Val
    -20                 -15                 -10

Gln Leu Asp Lys Arg Gly Pro Glu Thr Leu Cys Gly Ala Glu Leu Val
 -5                   1                   5                  10

Asp Ala Leu Gln Phe Val Cys Gly Asp Arg Gly Phe Tyr Phe Asn Lys
            15                  20                  25

Pro Thr Gly Tyr Gly Ser Ser Ser Arg Arg Ala Pro Gln Thr Gly Ile
            30                  35                  40

Val Asp Glu Cys Cys Phe Arg Ser Cys Asp Leu Arg Arg Leu Glu Met
        45                  50                  55

Tyr Cys Ala Pro Leu Lys Pro Ala Lys Ser Ala Lys Arg Ser Val Arg
 60                  65                  70                  75

Ala Gln Arg His Thr Asp Met Pro Lys Thr Gln Lys Glu Val His Leu
                80                  85                  90

Lys Asn Ala Ser Arg Gly Ser Ala Gly Asn Lys Asn Tyr Arg Met
            95                 100                 105
```